United States Patent
Miyazaki et al.

(10) Patent No.: US 11,866,471 B2
(45) Date of Patent: Jan. 9, 2024

(54) VARIANT AIM

(71) Applicant: Toru Miyazaki, Tokyo (JP)

(72) Inventors: Toru Miyazaki, Tokyo (JP); Satoko Arai, Tokyo (JP)

(73) Assignee: Toro Miyazaki, Tokyo (JP)

( * ) Notice: Subject to any disclaimer, the term of this patent is extended or adjusted under 35 U.S.C. 154(b) by 132 days.

(21) Appl. No.: 16/764,755

(22) PCT Filed: Oct. 9, 2018

(86) PCT No.: PCT/JP2018/037505
§ 371 (c)(1),
(2) Date: May 15, 2020

(87) PCT Pub. No.: WO2019/097898
PCT Pub. Date: May 23, 2019

(65) Prior Publication Data
US 2020/0399332 A1 Dec. 24, 2020

(30) Foreign Application Priority Data
Nov. 16, 2017 (JP) .................. 2017-220733

(51) Int. Cl.
| C07K 14/47 | (2006.01) |
| C12N 15/63 | (2006.01) |
| A61K 38/00 | (2006.01) |
| C07K 14/705 | (2006.01) |
| C12P 21/02 | (2006.01) |

(52) U.S. Cl.
CPC .... *C07K 14/4702* (2013.01); *C07K 14/70596* (2013.01); *C12N 15/63* (2013.01); *C12P 21/02* (2013.01); *A61K 38/00* (2013.01)

(58) Field of Classification Search
CPC .......... C07K 14/4702; C07K 14/70596; C07K 2319/02; C07K 2319/50; C12N 15/63; C12P 21/02; A61K 38/00
See application file for complete search history.

(56) References Cited

U.S. PATENT DOCUMENTS

| 6,046,314 A | 4/2000 | Gebe et al. |
| 2010/0331244 A1 | 12/2010 | Miyazaki |
| 2013/0115220 A1 | 5/2013 | Miyazaki |
| 2015/0094268 A1 | 4/2015 | Miyazaki |
| 2017/0172120 A1 | 6/2017 | Miyazaki |

FOREIGN PATENT DOCUMENTS

| CA | 3114869 A1 | 4/2020 |
| WO | WO-2010/140531 A1 | 12/2010 |
| WO | WO-2013/162021 A1 | 10/2013 |
| WO | WO-2015/119253 A1 | 8/2015 |

OTHER PUBLICATIONS

Arai et al., Obesity-associated autoantibody production requires AIM to retain the immunoglobulin M immune complex on follicular dendritic cells, *Cell Rep*. 3:1187-98 (2013).
Chappell et al., Structures of CD6 and Its Ligand CD166 Give Insight into Their Interaction, *Structure*. 23:1426-36 (2015).
GenBank Accession No. XP_001116945.1, Predicted: CD5 antigen-like [Macaca mulatta], Dec. 21, 2015.
GenBank Accession No. XP_003258693.1, Predicted: CD5 antigen-like [Nomascus leucogenys], May 13, 2015.
International Search Report, PCT/JP2018/037505, dated Dec. 11, 2018.
Kurokawa et al., Apoptosis inhibitor of macrophage (AIM) is required for obesity-associated recruitment of inflammatory macrophages into adipose tissue, *Proc. Natl. Acad. Sci. USA*. 108:12072-77 (2011).
Kurokawa et al., Macrophage-derived AIM is endocytosed into adipocytes and decreases lipid droplets via inhibition of fatty acid synthase activity, *Cell Metab*. 11:479-92 (2010).
Miyazaki et al., AIM associated with the IgM pentamer: attackers on stand-by at aircraft carrier, *Cell. Mol. Immunol*. 15:563-74 (2018).
Miyazaki et al., AIMing at metabolic syndrome, Towards the development of novel therapies for metabolic diseases via apoptosis inhibitor of macrophage (AIM), *Circ. J*. 75:2522-31 (2011).
Miyazaki et al., Increased susceptibility of thymocytes to apoptosis in mice lacking AIM, a novel murine macrophage-derived soluble factor belonging to the scavenger receptor cysteine-rich domain superfamily, *J. Exp. Med*. 189:413-22 (1999).
Resnick et al., The SRCR superfamily: a family reminiscent of the Ig superfamily, *Trends Biochem. Sci*. 19:5-8 (1994).
Sanjurjo et al., AIM/CD5L: a key protein in the control of immune homeostasis and inflammatory disease, *J. Leukoc. Biol*. 98:173-84 (2015).
Supplementary European Search Report, European Application No. 18877418, dated Jul. 12, 2021.
Yamazaki et al., A proteolytic modification of AIM promotes its renal excretion, *Sci. Rep*. 6:1-11 (2016).

*Primary Examiner* — Ganapathirama Raghu
(74) *Attorney, Agent, or Firm* — MARSHALL, GERSTEIN & BORUN LLP

(57) ABSTRACT

The present invention relates to the provision of a recombinant AIM that maintains functions, does not multimerize, and is not inactivated by IgM (e.g., a protein containing an amino acid sequence wherein cysteine at amino acid number 168 of the amino acid sequence shown in SEQ ID NO: 1 is substituted with another amino acid, and the like).

12 Claims, 6 Drawing Sheets

Specification includes a Sequence Listing.

Fig. 3

Signal Peptide
```
WT     MALLFSLILAICTRPGFLASPSG
2CS    MALLFSLILAICTRPGFLASPSG
3CS    MALLFSLILAICTRPGFLASPSG
2/3CS  MALLFSLILAICTRPGFLASPSG
```

SRCR1 domain
```
WT     VRLVGGLHRCEGRVEVEQKGQWGTVCDDGWDIKDVAVLCRELGCGAASGTPSGILYEP
2CS    VRLVGGLHRCEGRVEVEQKGQWGTVCDDGWDIKDVAVLCRELGCGAASGTPSGILYEP
3CS    VRLVGGLHRCEGRVEVEQKGQWGTVCDDGWDIKDVAVLCRELGCGAASGTPSGILYEP
2/3CS  VRLVGGLHRCEGRVEVEQKGQWGTVCDDGWDIKDVAVLCRELGCGAASGTPSGILYEP WT     PAEKEQKVLIQSVSCTGTEDTLAQCEQEEVYDCSHDEDAGASCE NPESSFSPVPEG
2CS    PAEKEQKVLIQSVSCTGTEDTLAQCEQEEVYDCSHDEDAGASCE NPESSFSPVPEG
3CS    PAEKEQKVLIQSVSCTGTEDTLAQCEQEEVYDCSHDEDAGASCE NPESSFSPVPEG
2/3CS  PAEKEQKVL-QSVSCTGTEDTLAQCEQEEVYDCSHDEDAGASCE NPESSFSPVPEG
```

SRCR2 domain
```
WT     VRLADGPGHCKGRVEVKHQNQWYTVCQTGWSLRAAKVVCRQLGCGRAVLTQKRCNKHA
2CS    VRLADGPGHCKGRVEVKHQNQWYTVCQTGWSLRAAKVVCRQLGCGRAVLTQKRSNKHA
3CS    VRLADGPGHCKGRVEVKHQNQWYTVCQTGWSLRAAKVVCRQLGCGRAVLTQKRCNKHA
2/3CS  VRLADGPGHCKGRVEVKHQNQWYTVCQTGWSLRAAKVVCRQLGCGRAVLTQKRSNKHA WT     YGRKPIWLSQMSCSGREATLQDCPSGPWGKNTCNHDEDTWVECE DPFD
2CS    YGRKPIWLSQMSCSGREATLQDCPSGPWGKNTCNHDEDTWVECE DPFD
3CS    YGRKPIWLSQMSCSGREATLQDCPSGPWGKNTCNHDEDTWVECE DPFD
2/3CS  YGRKPIWLSQMSCSGREATLQDCPSGPWGKNTCNHDEDTWVECE DPFD
```

SRCR3 domain
```
WT     LRLVGGDNLCSGRLEVLHKGVWGSVCDDNWGEKEDQVVCKQLGCGKSLSPSFRDRKCY
2CS    LRLVGGDNLCSGRLEVLHKGVWGSVCDDNWGEKEDQVVCKQLGCGKSLSPSFRDRKCY
3CS    LRLVGGDNLCSGRLEVLHKGVWGSVCDDNWGEKEDQVVCKQLGCGKSLSPSFRDRKSY
2/3CS  LRLVGGDNLCSGRLEVLHKGVWGSVCDDNWGEKEDQVVCKQLGCGKSLSPSFRDRKSY WT     GPGVGRIWLDNVRCSGEEQSLEQCQHRFWGFHDCTHQEDVAVICS G
2CS    GPGVGRIWLDNVRCSGEEQSLEQCQHRFWGFHDCTHQEDVAVICS G
3CS    GPGVGRIWLDNVRCSGEEQSLEQCQHRFWGFHDCTHQEDVAVICS G
2/3CS  GPGVGRIWLDNVRCSGEEQSLEQCQHRFWGFHDCTHQEDVAVICS G
```

Human AIM

Mouse AIM

Fig. 6

WT  MAPLFNLMLAILSIFVGSCFSESPTK
2CS MAPLFNLMLAILSIFVGSCFSESPTK

WT  VQLVGGAHRCEGRVEVEHNGQWGTVCDDGWDRRDVAVVCRELNCGAVIQTPRGASYQP
2CS VQLVGGAHRCEGRVEVEHNGQWGTVCDDGWDRRDVAVVCRELNCGAVIQTPRGASYQP

WT  PASEQRVLIQGVDCNGTEDTLAQCELNYDVFDCSHEEDAGAQCE NPDSDLLFIPED
2CS PASEQRVLIQGVDCNGTEDTLAQCELNYDVFDCSHEEDAGAQCE NPDSDLLFIPED

WT  VRLVDGPGHCQGRVEVLHQSQWSTVCKAGWNLQVSKVVCRQLGCGRALLTYGSCNKNT
2CS VRLVDGPGHCQGRVEVLHQSQWSTVCKAGWNLQVSKVVCRQLGCGRALLTYGSSNKNT

WT  QGKGPIWMGKMSCSGQEANLRSCLISRLENNCTHGEDTWMECE DPFE
2CS QGKGPIWMGKMSCSGQEANLRSCLISRLENNCTHGEDTWMECE DPFE

WT  LKLVGGDTPCSGRLEVLHKGSWGSVCDDNWGEKEDQVVCKQLGCGKSLHPSPKTRKIY
2CS LKLVGGDTPCSGRLEVLHKGSWGSVCDDNWGEKEDQVVCKQLGCGKSLHPSPKTRKIY

WT  GPGAGRIWLDDVNCSGKEQSLEFCRHRLWGYHDCTHKEDVEVICT DEDV
2CS GPGAGRIWLDDVNCSGKEQSLEFCRHRLWGYHDCTHKEDVEVICT DEDV

SEQUENCE LISTING

<160> NUMBER OF SEQ ID NOS: 14

<210> SEQ ID NO 1
<211> LENGTH: 324
<212> TYPE: PRT
<213> ORGANISM: Homo sapiens

<400> SEQUENCE: 1

Val Arg Leu Val Gly Gly Leu His Arg Cys Glu Gly Arg Val Glu Val
1               5                   10                  15

Glu Gln Lys Gly Gln Trp Gly Thr Val Cys Asp Asp Gly Trp Asp Ile
            20                  25                  30

Lys Asp Val Ala Val Leu Cys Arg Glu Leu Gly Cys Gly Ala Ala Ser
        35                  40                  45

Gly Thr Pro Ser Gly Ile Leu Tyr Glu Pro Ala Glu Lys Glu Gln
    50                  55                  60

Lys Val Leu Ile Gln Ser Val Ser Cys Thr Gly Thr Glu Asp Thr Leu
65                  70                  75                  80

Ala Gln Cys Glu Gln Glu Glu Val Tyr Asp Cys Ser His Asp Glu Asp
            85                  90                  95

Ala Gly Ala Ser Cys Glu Asn Pro Glu Ser Ser Phe Ser Pro Val Pro
        100                 105                 110

Glu Gly Val Arg Leu Ala Asp Gly Pro Gly His Cys Lys Gly Arg Val
        115                 120                 125

Glu Val Lys His Gln Asn Gln Trp Tyr Thr Val Cys Gln Thr Gly Trp
    130                 135                 140

Ser Leu Arg Ala Ala Lys Val Val Cys Arg Gln Leu Gly Cys Gly Arg
145                 150                 155                 160

Ala Val Leu Thr Gln Lys Arg Cys Asn Lys His Ala Tyr Gly Arg Lys
                165                 170                 175

Pro Ile Trp Leu Ser Gln Met Ser Cys Ser Gly Arg Glu Ala Thr Leu
            180                 185                 190

Gln Asp Cys Pro Ser Gly Pro Trp Gly Lys Asn Thr Cys Asn His Asp
        195                 200                 205

Glu Asp Thr Trp Val Glu Cys Glu Asp Pro Phe Asp Leu Arg Leu Val
    210                 215                 220

Gly Gly Asp Asn Leu Cys Ser Gly Arg Leu Glu Val Leu His Lys Gly
225                 230                 235                 240

Val Trp Gly Ser Val Cys Asp Asp Asn Trp Gly Glu Lys Glu Asp Gln
                245                 250                 255

Val Val Cys Lys Gln Leu Gly Cys Gly Lys Ser Leu Ser Pro Ser Phe
            260                 265                 270

Arg Asp Arg Lys Cys Tyr Gly Pro Gly Val Gly Arg Ile Trp Leu Asp
        275                 280                 285

Asn Val Arg Cys Ser Gly Glu Glu Gln Ser Leu Glu Gln Cys Gln His
    290                 295                 300

Arg Phe Trp Gly Phe His Asp Cys Thr His Gln Glu Asp Val Ala Val
305                 310                 315                 320

Ile Cys Ser Gly

<210> SEQ ID NO 2
<211> LENGTH: 326
<212> TYPE: PRT
<213> ORGANISM: Mus musculus

<400> SEQUENCE: 2

Val Gln Leu Val Gly Gly Ala His Arg Cys Glu Gly Arg Val Glu Val
1               5                   10                  15

Glu His Asn Gly Gln Trp Gly Thr Val Cys Asp Asp Gly Trp Asp Arg
            20                  25                  30

Arg Asp Val Ala Val Val Cys Arg Glu Leu Asn Cys Gly Ala Val Ile
            35                  40                  45

Gln Thr Pro Arg Gly Ala Ser Tyr Gln Pro Pro Ala Ser Glu Gln Arg
        50                  55                  60

Val Leu Ile Gln Gly Val Asp Cys Asn Gly Thr Glu Asp Thr Leu Ala
65                  70                  75                  80

Gln Cys Glu Leu Asn Tyr Asp Val Phe Asp Cys Ser His Glu Glu Asp
                85                  90                  95

Ala Gly Ala Gln Cys Glu Asn Pro Asp Ser Asp Leu Leu Phe Ile Pro
            100                 105                 110

Glu Asp Val Arg Leu Val Asp Gly Pro Gly His Cys Gln Gly Arg Val
        115                 120                 125

Glu Val Leu His Gln Ser Gln Trp Ser Thr Val Cys Lys Ala Gly Trp
    130                 135                 140

Asn Leu Gln Val Ser Lys Val Val Cys Arg Gln Leu Gly Cys Gly Arg
145                 150                 155                 160

Ala Leu Leu Thr Tyr Gly Ser Cys Asn Lys Asn Thr Gln Gly Lys Gly
                165                 170                 175

Pro Ile Trp Met Gly Lys Met Ser Cys Ser Gly Gln Glu Ala Asn Leu
            180                 185                 190

Arg Ser Cys Leu Leu Ser Arg Leu Glu Asn Asn Cys Thr His Gly Glu
        195                 200                 205

Asp Thr Trp Met Glu Cys Glu Asp Pro Phe Glu Leu Lys Leu Val Gly
    210                 215                 220

Gly Asp Thr Pro Cys Ser Gly Arg Leu Glu Val Leu His Lys Gly Ser
225                 230                 235                 240

Trp Gly Ser Val Cys Asp Asp Asn Trp Gly Glu Lys Glu Asp Gln Val
                245                 250                 255

Val Cys Lys Gln Leu Gly Cys Gly Lys Ser Leu His Pro Ser Pro Lys
            260                 265                 270

Thr Arg Lys Ile Tyr Gly Pro Gly Ala Gly Arg Ile Trp Leu Asp Asp
        275                 280                 285

Val Asn Cys Ser Gly Lys Glu Gln Ser Leu Glu Phe Cys Arg His Arg
    290                 295                 300

Leu Trp Gly Tyr His Asp Cys Thr His Lys Glu Asp Val Glu Val Ile
305                 310                 315                 320

Cys Thr Asp Phe Asp Val
                325

<210> SEQ ID NO 3
<211> LENGTH: 324
<212> TYPE: PRT
<213> ORGANISM: Homo sapiens

<400> SEQUENCE: 3

Val Arg Leu Val Gly Gly Leu His Arg Cys Glu Gly Arg Val Glu Val
1               5                   10                  15

Glu Gln Lys Gly Gln Trp Gly Thr Val Cys Asp Asp Gly Trp Asp Ile
            20                  25                  30

Lys Asp Val Ala Val Leu Cys Arg Glu Leu Gly Cys Gly Ala Ala Ser

```
            35                  40                  45
Gly Thr Pro Ser Gly Ile Leu Tyr Glu Pro Ala Glu Lys Glu Gln
 50                  55                  60
Lys Val Leu Ile Gln Ser Val Ser Cys Thr Gly Thr Glu Asp Thr Leu
 65                  70                  75                  80
Ala Gln Cys Glu Gln Glu Glu Val Tyr Asp Cys Ser His Asp Glu Asp
                 85                  90                  95
Ala Gly Ala Ser Cys Glu Asn Pro Glu Ser Ser Phe Ser Pro Val Pro
            100                 105                 110
Glu Gly Val Arg Leu Ala Asp Gly Pro Gly His Cys Lys Gly Arg Val
            115                 120                 125
Glu Val Lys His Gln Asn Gln Trp Tyr Thr Val Cys Gln Thr Gly Trp
            130                 135                 140
Ser Leu Arg Ala Ala Lys Val Val Cys Arg Gln Leu Gly Cys Gly Arg
145                 150                 155                 160
Ala Val Leu Thr Gln Lys Arg Ser Asn Lys His Ala Tyr Gly Arg Lys
                165                 170                 175
Pro Ile Trp Leu Ser Gln Met Ser Cys Ser Gly Arg Glu Ala Thr Leu
            180                 185                 190
Gln Asp Cys Pro Ser Gly Pro Trp Gly Lys Asn Thr Cys Asn His Asp
            195                 200                 205
Glu Asp Thr Trp Val Glu Cys Glu Asp Pro Phe Asp Leu Arg Leu Val
210                 215                 220
Gly Gly Asp Asn Leu Cys Ser Gly Arg Leu Glu Val Leu His Lys Gly
225                 230                 235                 240
Val Trp Gly Ser Val Cys Asp Asp Asn Trp Gly Lys Glu Asp Gln
                245                 250                 255
Val Val Cys Lys Gln Leu Gly Cys Gly Lys Ser Leu Ser Pro Ser Phe
            260                 265                 270
Arg Asp Arg Lys Cys Tyr Gly Pro Gly Val Gly Arg Ile Trp Leu Asp
            275                 280                 285
Asn Val Arg Cys Ser Gly Glu Glu Gln Ser Leu Glu Gln Cys Gln His
            290                 295                 300
Arg Phe Trp Gly Phe His Asp Cys Thr His Gln Glu Asp Val Ala Val
305                 310                 315                 320
Ile Cys Ser Gly

<210> SEQ ID NO 4
<211> LENGTH: 324
<212> TYPE: PRT
<213> ORGANISM: Homo sapiens

<400> SEQUENCE: 4

Val Arg Leu Val Gly Gly Leu His Arg Cys Glu Gly Arg Val Glu Val
 1               5                  10                  15
Glu Gln Lys Gly Gln Trp Gly Thr Val Cys Asp Asp Gly Trp Asp Ile
                 20                  25                  30
Lys Asp Val Ala Val Leu Cys Arg Glu Leu Gly Cys Gly Ala Ala Ser
            35                  40                  45
Gly Thr Pro Ser Gly Ile Leu Tyr Glu Pro Ala Glu Lys Glu Gln
 50                  55                  60
Lys Val Leu Ile Gln Ser Val Ser Cys Thr Gly Thr Glu Asp Thr Leu
 65                  70                  75                  80
Ala Gln Cys Glu Gln Glu Glu Val Tyr Asp Cys Ser His Asp Glu Asp
```

```
            85                  90                  95
Ala Gly Ala Ser Cys Glu Asn Pro Glu Ser Ser Phe Ser Pro Val Pro
            100                 105                 110

Glu Gly Val Arg Leu Ala Asp Gly Pro Gly His Cys Lys Gly Arg Val
            115                 120                 125

Glu Val Lys His Gln Asn Gln Trp Tyr Thr Val Cys Gln Thr Gly Trp
            130                 135                 140

Ser Leu Arg Ala Ala Lys Val Val Cys Arg Gln Leu Gly Cys Gly Arg
145                 150                 155                 160

Ala Val Leu Thr Gln Lys Arg Cys Asn Lys His Ala Tyr Gly Arg Lys
            165                 170                 175

Pro Ile Trp Leu Ser Gln Met Ser Cys Ser Gly Arg Glu Ala Thr Leu
            180                 185                 190

Gln Asp Cys Pro Ser Gly Pro Trp Gly Lys Asn Thr Cys Asn His Asp
            195                 200                 205

Glu Asp Thr Trp Val Glu Cys Glu Asp Pro Phe Asp Leu Arg Leu Val
            210                 215                 220

Gly Gly Asp Asn Leu Cys Ser Gly Arg Leu Glu Val Leu His Lys Gly
225                 230                 235                 240

Val Trp Gly Ser Val Cys Asp Asp Asn Trp Gly Lys Glu Asp Gln
            245                 250                 255

Val Val Cys Lys Gln Leu Gly Cys Gly Lys Ser Leu Ser Pro Ser Phe
            260                 265                 270

Arg Asp Arg Lys Ser Tyr Gly Pro Gly Val Gly Arg Ile Trp Leu Asp
            275                 280                 285

Asn Val Arg Cys Ser Gly Glu Glu Gln Ser Leu Glu Gln Cys Gln His
            290                 295                 300

Arg Phe Trp Gly Phe His Asp Cys Thr His Gln Glu Asp Val Ala Val
305                 310                 315                 320

Ile Cys Ser Gly

<210> SEQ ID NO 5
<211> LENGTH: 324
<212> TYPE: PRT
<213> ORGANISM: Homo sapiens

<400> SEQUENCE: 5

Val Arg Leu Val Gly Gly Leu His Arg Cys Glu Gly Arg Val Glu Val
1               5                   10                  15

Glu Gln Lys Gly Gln Trp Gly Thr Val Cys Asp Asp Gly Trp Asp Ile
            20                  25                  30

Lys Asp Val Ala Val Leu Cys Arg Glu Leu Gly Cys Gly Ala Ala Ser
            35                  40                  45

Gly Thr Pro Ser Gly Ile Leu Tyr Glu Pro Pro Ala Glu Lys Glu Gln
            50                  55                  60

Lys Val Leu Ile Gln Ser Val Ser Cys Thr Gly Thr Glu Asp Thr Leu
65                  70                  75                  80

Ala Gln Cys Glu Gln Glu Glu Val Tyr Asp Cys Ser His Asp Glu Asp
            85                  90                  95

Ala Gly Ala Ser Cys Glu Asn Pro Glu Ser Ser Phe Ser Pro Val Pro
            100                 105                 110

Glu Gly Val Arg Leu Ala Asp Gly Pro Gly His Cys Lys Gly Arg Val
            115                 120                 125

Glu Val Lys His Gln Asn Gln Trp Tyr Thr Val Cys Gln Thr Gly Trp
```

```
                130                 135                 140
Ser Leu Arg Ala Ala Lys Val Cys Arg Gln Leu Gly Cys Gly Arg
145                 150                 155                 160

Ala Val Leu Thr Gln Lys Arg Ser Asn Lys His Ala Tyr Gly Arg Lys
                165                 170                 175

Pro Ile Trp Leu Ser Gln Met Ser Cys Ser Gly Arg Glu Ala Thr Leu
                180                 185                 190

Gln Asp Cys Pro Ser Gly Pro Trp Gly Lys Asn Thr Cys Asn His Asp
            195                 200                 205

Glu Asp Thr Trp Val Glu Cys Glu Asp Pro Phe Asp Leu Arg Leu Val
        210                 215                 220

Gly Gly Asp Asn Leu Cys Ser Gly Arg Leu Glu Val Leu His Lys Gly
225                 230                 235                 240

Val Trp Gly Ser Val Cys Asp Asp Asn Trp Gly Glu Lys Glu Asp Gln
                245                 250                 255

Val Val Cys Lys Gln Leu Gly Cys Gly Lys Ser Leu Ser Pro Ser Phe
                260                 265                 270

Arg Asp Arg Lys Ser Tyr Gly Pro Gly Val Gly Arg Ile Trp Leu Asp
            275                 280                 285

Asn Val Arg Cys Ser Gly Glu Glu Gln Ser Leu Glu Gln Cys Gln His
        290                 295                 300

Arg Phe Trp Gly Phe His Asp Cys Thr His Gln Glu Asp Val Ala Val
305                 310                 315                 320

Ile Cys Ser Gly

<210> SEQ ID NO 6
<211> LENGTH: 326
<212> TYPE: PRT
<213> ORGANISM: Mus musculus

<400> SEQUENCE: 6

Val Gln Leu Val Gly Gly Ala His Arg Cys Glu Gly Arg Val Glu Val
1               5                   10                  15

Glu His Asn Gly Gln Trp Gly Thr Val Cys Asp Asp Gly Trp Asp Arg
                20                  25                  30

Arg Asp Val Ala Val Val Cys Arg Glu Leu Asn Cys Gly Ala Val Ile
            35                  40                  45

Gln Thr Pro Arg Gly Ala Ser Tyr Gln Pro Pro Ala Ser Glu Gln Arg
        50                  55                  60

Val Leu Ile Gln Gly Val Asp Cys Asn Gly Thr Glu Asp Thr Leu Ala
65                  70                  75                  80

Gln Cys Glu Leu Asn Tyr Asp Val Phe Asp Cys Ser His Glu Glu Asp
                85                  90                  95

Ala Gly Ala Gln Cys Glu Asn Pro Asp Ser Asp Leu Leu Phe Ile Pro
            100                 105                 110

Glu Asp Val Arg Leu Val Asp Gly Pro Gly His Cys Gln Gly Arg Val
        115                 120                 125

Glu Val Leu His Gln Ser Gln Trp Ser Thr Val Cys Lys Ala Gly Trp
130                 135                 140

Asn Leu Gln Val Ser Lys Val Val Cys Arg Gln Leu Gly Cys Gly Arg
145                 150                 155                 160

Ala Leu Leu Thr Tyr Gly Ser Ser Asn Lys Asn Thr Gln Gly Lys Gly
                165                 170                 175

Pro Ile Trp Met Gly Lys Met Ser Cys Ser Gly Gln Glu Ala Asn Leu
```

```
                    180                 185                 190
Arg Ser Cys Leu Leu Ser Arg Leu Glu Asn Asn Cys Thr His Gly Glu
            195                 200                 205

Asp Thr Trp Met Glu Cys Glu Asp Pro Phe Glu Leu Lys Leu Val Gly
        210                 215                 220

Gly Asp Thr Pro Cys Ser Gly Arg Leu Glu Val Leu His Lys Gly Ser
225                 230                 235                 240

Trp Gly Ser Val Cys Asp Asp Asn Trp Gly Lys Glu Asp Gln Val
                    245                 250                 255

Val Cys Lys Gln Leu Gly Cys Gly Lys Ser Leu His Pro Ser Pro Lys
                260                 265                 270

Thr Arg Lys Ile Tyr Gly Pro Gly Ala Gly Arg Ile Trp Leu Asp Asp
            275                 280                 285

Val Asn Cys Ser Gly Lys Glu Gln Ser Leu Glu Phe Cys Arg His Arg
        290                 295                 300

Leu Trp Gly Tyr His Asp Cys Thr His Lys Glu Asp Val Glu Val Ile
305                 310                 315                 320

Cys Thr Asp Phe Asp Val
                325
```

<210> SEQ ID NO 7
<211> LENGTH: 23
<212> TYPE: PRT
<213> ORGANISM: Homo sapiens

<400> SEQUENCE: 7

```
Met Ala Leu Leu Phe Ser Leu Ile Leu Ala Ile Cys Thr Arg Pro Gly
1               5                   10                  15

Phe Leu Ala Ser Pro Ser Gly
            20
```

<210> SEQ ID NO 8
<211> LENGTH: 26
<212> TYPE: PRT
<213> ORGANISM: Mus musculus

<400> SEQUENCE: 8

```
Met Ala Pro Leu Phe Asn Leu Met Leu Ala Ile Leu Ser Ile Phe Val
1               5                   10                  15

Gly Ser Cys Phe Ser Glu Ser Pro Thr Lys
            20                  25
```

<210> SEQ ID NO 9
<211> LENGTH: 1044
<212> TYPE: DNA
<213> ORGANISM: Homo sapiens

<400> SEQUENCE: 9

```
atggctctgc tcttcagcct catcctcgcc atctgcacca gacccggctt cctcgccagc    60
cccagcggag tgagactggt cggaggcctg cacagatgtg aaggccgcgt cgaggtggag   120
cagaagggcc agtggggcac cgtctgcgac gacggctggg acatcaagga cgtggctgtc   180
ctctgccgcg agctgggatg cggtgctgcc agcggcacgc ccagcggcat cctgtacgag   240
cctcccgcag agaaggagca gaaggtcctg atccagagcg tcagctgcac aggcaccgag   300
gacacactgg ctcagtgtga gcaggaggaa gtctacgact gtagccacga cgaggacgct   360
ggcgcatcct gcgagaaccc cgagagctcc ttcagccccg tgcccgaggg cgtcagactg   420
```

| | |
|---|---|
| gctgacggcc ctggccactg caagggcaga gtcgaggtga agcaccagaa ccagtggtac | 480 |
| accgtgtgcc agaccggctg gagcctcaga gccgcaaagg tcgtctgccg gcagctgggc | 540 |
| tgtggcaggg ctgtactgac tcagaagcgc tgcaacaagc acgcctacgg ccgcaagccc | 600 |
| atctggctca gccagatgag ctgcagcggc cgcgaggcaa ccctgcagga ctgccccagc | 660 |
| ggcccttggg gcaagaacac ctgcaaccat gacgaggaca cgtgggtcga gtgtgaagat | 720 |
| cccttcgact tgcgcctcgt cggaggagac aacctctgca cggccgcct cgaggtgctg | 780 |
| cacaagggcg tctggggcag cgtctgcgac gacaactggg gcgagaagga ggaccaggtg | 840 |
| gtatgcaagc aactgggctg tggcaagtcc ctcagcccca gcttccgcga ccgcaagtgc | 900 |
| tacggtcccg gcgtcggcag aatctggctg gacaacgtcc gctgcagcgg cgaggagcag | 960 |
| agcctcgagc agtgccagca ccgcttctgg ggcttccacg actgcaccca ccaggaggac | 1020 |
| gtcgctgtca tctgcagcgg ctag | 1044 |

<210> SEQ ID NO 10
<211> LENGTH: 1059
<212> TYPE: DNA
<213> ORGANISM: Mus musculus

<400> SEQUENCE: 10

| | |
|---|---|
| atggctccat tgttcaactt gatgctggcc atcttgagca ttttgttgg atcgtgtttt | 60 |
| tcagagtctc caaccaaagt gcagctagtg ggaggtgccc accgctgtga agggcgagtg | 120 |
| gaggtggaac acaatggcca gtggggact gtgtgtgatg atggctggga ccggcgtgat | 180 |
| gtggctgtgg tgtgccgaga gctcaattgt ggagcagtca tccaaacccc gcgtggcgca | 240 |
| tcatatcagc caccagcatc agagcaaaga gttcttattc aaggggttga ctgcaacgga | 300 |
| acggaagaca cgttggctca atgtgagcta aattacgatg ttttgactg ctcacatgaa | 360 |
| gaagatgctg ggcacagtg tgagaaccca gacagtgacc tcctcttcat tccagaggat | 420 |
| gtgcgtctag tagatggccc ggggcactgc cagggtcgag tggaggtgct ccaccagtcc | 480 |
| cagtggagca ctgtgtgtaa agcaggctgg aacttacagg tctcaaaggt ggtgtgcagg | 540 |
| cagctcgggt gtgggcgggc attactgacc tacggaagct gcaacaagaa tactcagggc | 600 |
| aaaggaccca tctggatggg caagatgtcg tgttctggac aagaagcaaa ccttcggtct | 660 |
| tgccttttga gtcgtttgga gaacaactgt acccatggcg aggacacatg gatgaatgt | 720 |
| gaagatcctt ttgagctgaa gctggtggga ggagacaccc cctgctctgg gaggttggag | 780 |
| gtgctgcaca ggggttcctg gggctccgtc tgtgatgaca ctggggaga aaggaggac | 840 |
| caagtggtct gcaagcaact gggttgtggg aagtccctcc atccatcccc caaaacccgg | 900 |
| aaaatctatg ggcctgggc aggccgcatc tggctggatg acgtcaactg ctcagggaag | 960 |
| gaacagtctc tggagttctg ccggcacagg ttgtgggggt accacgactg tacccacaag | 1020 |
| gaagatgtgg aggtgatctg cacagacttt gatgtgtga | 1059 |

<210> SEQ ID NO 11
<211> LENGTH: 1044
<212> TYPE: DNA
<213> ORGANISM: Homo sapiens

<400> SEQUENCE: 11

| | |
|---|---|
| atggctctgc tcttcagcct catcctcgcc atctgcacca gacccggctt cctcgccagc | 60 |
| cccagcggag tgagactggt cggaggcctg cacagatgtg aaggccgcgt cgaggtggag | 120 |
| cagaagggcc agtggggcac cgtctgcgac gacggctggg acatcaagga cgtggctgtc | 180 |

```
ctctgccgcg agctgggatg cggtgctgcc agcggcacgc ccagcggcat cctgtacgag    240
cctcccgcag agaaggagca gaaggtcctg atccagagcg tcagctgcac aggcaccgag    300
gacacactgg ctcagtgtga gcaggaggaa gtctacgact gtagccacga cgaggacgct    360
ggcgcatcct gcgagaaccc cgagagctcc ttcagcccg tgcccgaggg cgtcagactg     420
gctgacggcc ctggccactg caagggcaga gtcgaggtga agcaccagaa ccagtggtac    480
accgtgtgcc agaccggctg gagcctcaga gccgcaaagg tcgtctgccg gcagctgggc    540
tgtggcaggg ctgtactgac tcagaagcgc tccaacaagc acgcctacgg ccgcaagccc    600
atctggctca gccagatgag ctgcagcggc cgcgaggcaa ccctgcagga ctgccccagc    660
ggcccttggg gcaagaacac ctgcaaccat gacgaggaca cgtgggtcga gtgtgaagat    720
cccttcgact gcgcctcgt cggaggagac aacctctgca gcggccgcct cgaggtgctg     780
cacaagggcg tctggggcag cgtctgcgac gacaactggg gcgagaagga ggaccaggtg    840
gtatgcaagc aactgggctg tggcaagtcc ctcagcccca gcttccgcga ccgcaagtgc    900
tacggtcccg gcgtcggcag aatctggctg gacaacgtcc gctgcagcgg cgaggagcag    960
agcctcgagc agtgccagca ccgcttctgg ggcttccacg actgcaccca ccaggaggac   1020
gtcgctgtca tctgcagcgg ctag                                          1044
```

<210> SEQ ID NO 12
<211> LENGTH: 1044
<212> TYPE: DNA
<213> ORGANISM: Homo sapiens

<400> SEQUENCE: 12

```
atggctctgc tcttcagcct catcctcgcc atctgcacca gacccggctt cctcgccagc     60
cccagcggag tgagactggt cggaggcctg cacagatgtg aaggccgcgt cgaggtggag    120
cagaagggcc agtggggcac cgtctgcgac gacggctggg acatcaagga cgtggctgtc    180
ctctgccgcg agctgggatg cggtgctgcc agcggcacgc ccagcggcat cctgtacgag    240
cctcccgcag agaaggagca gaaggtcctg atccagagcg tcagctgcac aggcaccgag    300
gacacactgg ctcagtgtga gcaggaggaa gtctacgact gtagccacga cgaggacgct    360
ggcgcatcct gcgagaaccc cgagagctcc ttcagcccg tgcccgaggg cgtcagactg     420
gctgacggcc ctggccactg caagggcaga gtcgaggtga agcaccagaa ccagtggtac    480
accgtgtgcc agaccggctg gagcctcaga gccgcaaagg tcgtctgccg gcagctgggc    540
tgtggcaggg ctgtactgac tcagaagcgc tgcaacaagc acgcctacgg ccgcaagccc    600
atctggctca gccagatgag ctgcagcggc cgcgaggcaa ccctgcagga ctgccccagc    660
ggcccttggg gcaagaacac ctgcaaccat gacgaggaca cgtgggtcga gtgtgaagat    720
cccttcgact gcgcctcgt cggaggagac aacctctgca gcggccgcct cgaggtgctg     780
cacaagggcg tctggggcag cgtctgcgac gacaactggg gcgagaagga ggaccaggtg    840
gtatgcaagc aactgggctg tggcaagtcc ctcagcccca gcttccgcga ccgcaagtcc    900
tacggtcccg gcgtcggcag aatctggctg gacaacgtcc gctgcagcgg cgaggagcag    960
agcctcgagc agtgccagca ccgcttctgg ggcttccacg actgcaccca ccaggaggac   1020
gtcgctgtca tctgcagcgg ctag                                          1044
```

<210> SEQ ID NO 13
<211> LENGTH: 1044
<212> TYPE: DNA

<213> ORGANISM: Homo sapiens

<400> SEQUENCE: 13

```
atggctctgc tcttcagcct catcctcgcc atctgcacca gacccggctt cctcgccagc    60
cccagcggag tgagactggt cggaggcctg cacagatgtg aaggccgcgt cgaggtggag   120
cagaagggcc agtggggcac cgtctgcgac gacggctggg acatcaagga cgtggctgtc   180
ctctgccgcg agctgggatg cggtgctgcc agcggcacgc ccagcggcat cctgtacgag   240
cctcccgcag agaaggagca aaggtcctg atccagagcg tcagctgcac aggcaccgag   300
gacacactgg ctcagtgtga gcaggaggaa gtctacgact gtagccacga cgaggacgct   360
ggcgcatcct gcgagaaccc cgagagctcc ttcagccccg tgcccgaggg cgtcagactg   420
gctgacggcc ctggccactg caagggcaga gtcgaggtga agcaccagaa ccagtggtac   480
accgtgtgcc agaccggctg gagcctcaga gccgcaaagg tcgtctgccg gcagctgggc   540
tgtggcaggg ctgtactgac tcagaagcgc tccaacaagc acgcctacgg ccgcaagccc   600
atctggctca gccagatgag ctgcagcggc cgcgaggcaa ccctgcagga ctgccccagc   660
ggcccttggg gcaagaacac ctgcaaccat gacgaggaca cgtgggtcga gtgtgaagat   720
cccttcgact tgcgcctcgt cggaggagac aacctctgca gcggccgcct cgaggtgctg   780
cacaagggcg tctggggcag cgtctgcgac gacaactggg gcgagaagga ggaccaggtg   840
gtatgcaagc aactgggctg tggcaagtcc ctcagcccca gcttcgcgca ccgcaagtcc   900
tacggtcccg cgtcggcag aatctggctg gacaacgtcc gctgcagcgg cgaggagcag   960
agcctcgagc agtgccagca ccgcttctgg ggcttccacg actgcaccca ccaggaggac  1020
gtcgctgtca tctgcagcgg ctag                                         1044
```

<210> SEQ ID NO 14
<211> LENGTH: 1059
<212> TYPE: DNA
<213> ORGANISM: Mus musculus

<400> SEQUENCE: 14

```
atggctccat tgttcaactt gatgctggcc atcttgagca tttttgttgg atcgtgtttt    60
tcagagtctc caaccaaagt gcagctagtg ggaggtgccc accgctgtga agggcgagtg   120
gaggtggaac acaatggcca gtgggggact gtgtgtgatg atggctggga ccggcgtgat   180
gtggctgtgg tgtgccgaga gctcaattgt ggagcagtca tccaaacccc gcgtggcgca   240
tcatatcagc caccagcatc agagcaaaga gttcttattc aaggggttga ctgcaacgga   300
acggaagaca cgttggctca atgtgagcta aattacgatg tttttgactg ctcacatgaa   360
gaagatgctg gggcacagtg tgagaaccca gacagtgacc tcctcttcat tccagaggat   420
gtgcgtctag tagatggccc ggggcactgc cagggtcgag tggaggtgct ccaccagtcc   480
cagtggagca ctgtgtgtaa agcaggctgg aacttacagg tctcaaaggt ggtgtgcagg   540
cagctcgggt gtgggcgggc attactgacc tacggaagct ccaacaagaa tactcagggc   600
aaaggaccca tctggatggg caagatgtcg tgttctggac aagaagcaaa ccttcggtct   660
tgccttttga gtcgtttgga gaacaactgt acccatggcg aggacacatg gatggaatgt   720
gaagatcctt ttgagctgaa gctggtggga ggagacaccc cctgctctgg gaggttggag   780
gtgctgcaca agggttcctg gggctccgtc tgtgatgaca ctggggaga aaggaggac   840
caagtggtct gcaagcaact gggttgtggg aagtccctcc atccatcccc caaaacccgg   900
```

```
aaaatctatg ggcctggggc aggccgcatc tggctggatg acgtcaactg ctcagggaag      960
gaacagtctc tggagttctg ccggcacagg ttgtgggggt accacgactg tacccacaag     1020
gaagatgtgg aggtgatctg cacagacttt gatgtgtga                            1059
```

VARIANT AIM

CROSS REFERENCE TO RELATED APPLICATIONS

This application is a U.S. National Stage of International Application No. PCT/JP2018/037505, filed Oct. 9, 2018, which claims the benefit of priority from Japanese Patent Application No. 2017-220733, filed Nov. 16, 2017. The entire contents of these applications are incorporated herein by reference in their entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "55684_Seqlisting.txt," 26,676 bytes, created on May 14, 2020.

TECHNICAL FIELD

The present invention relates to a mutant AIM, a nucleic acid encoding the mutant AIM, an expression vector containing the nucleic acid, a host cell containing the expression vector, a production method of a mutant AIM using the host cell, and a pharmaceutical composition containing the mutant AIM.

BACKGROUND ART

AIM (apoptosis inhibitor of macrophage, or CD5L) is a factor which is specifically produced by a macrophage identified by the present inventors and suppresses apoptosis of the macrophage itself (non-patent document 1), and association with several diseases has been suggested so far. For example, the blood concentration of AIM increases with obesity, and AIM is taken up by adipocytes due to CD36-mediated endocytosis and induces lipolysis of accumulated neutral fats, which suggests relationship with antiobesity (non-patent document 2). AIM releases free fatty acid from adipocytes by lipolysis of neutral fats, and the released fatty acid induces/maintains chronic inflammation in adipose tissue via stimulation of toll-like receptors. Metabolic syndrome is based on the acquisition of insulin resistance associated with obesity. Since chronic inflammation in adipose tissue is important, AIM is said to be associated with metabolic syndrome (non-patent document 3). The present inventors also clarified that AIM suppresses the differentiation of fat progenitor cells into mature adipocytes and induces the decomposition of fat droplets in adipocytes, and reported the possibility of application of AIM to obesity (patent document 1). Furthermore, the present inventors clarified that obese AIM knockout (KO) mice loaded with a high-calorie diet show pathology similar to human NASH pathology, such as obesity, fatty liver, fibrosis of liver parenchyma, and carcinogenesis, and reported the possibility of application of AIM to liver diseases (patent document 2). In addition, the present inventors clarified that AIM KO mice that underwent bilateral transient renal ischemia reperfusion developed acute renal failure, followed by the accumulation of necrotic renal tubular cells and the accompanying rapid progression of renopathy, and exacerbation of the systemic condition, and a high frequency of death was confirmed. The inventors showed that when AIM was administered to the AIM KO mice, BUN level was improved, renal function was rapidly improved, and systemic symptoms and mortality were also improved, and reported the possibility of the treatment of acute renal failure and the prophylaxis or treatment of chronic renal diseases by the supplementation of AIM (patent document 3). Also, the inventors reported that in blood, AIM forms a complex with IgM pentamer in the Fc region, which protects AIM from renal filtration and maintains high level of blood AIM (non-patent documents 4, 5).

Generally, when a protein having a pharmacological effect is used as a pharmaceutical product, it is necessary to prepare a uniform protein that satisfies the conditions such as maintenance of function, absence of coagulation and the like. A typical method for preparing a protein is a method including culturing a cell into which an expression vector having a nucleic acid encoding a desired protein has been introduced, and isolating and purifying a recombinant protein secreted inside the cell or secreted into the culture medium from the cell. In the present method, *Escherichia coli* is preferably used as a host cell because it is easy to handle in gene transfer, culturing and the like. However, problems may occur during preparation of protein under conditions different from the original environment. For example, eukaryote-derived proteins may form intramolecular disulfide bonds between cysteines when forming higher-order structures. When such a protein is prepared by transforming *Escherichia coli*, the formation of disulfide bond is prevented since the cytoplasm of *Escherichia coli* is under strong reducing conditions. As a result, problems may occur in that the original higher-order structure is not reproduced, the purified recombinant protein loses its original function or exhibits toxicity, and the like. When a mammalian cell is used as a host cell and the target protein is expressed at a concentration higher than that at which the protein is normally present in the cell, the recombinant proteins may form a multimer by disulfide bond, which may affect purification of the recombinant protein or pharmacokinetics in vivo. Since AIM contains 3 scavenger receptor cysteine-rich (SRCR) domains consisting of about 100 amino acids containing many cysteines, *Escherichia coli* is not suitable as a host cell when recombinant AIM is produced, and even when mammalian cells are used, it was necessary to verify whether or not the recombinant AIM is multimerized, and when multimerization is confirmed, a means for preventing the multimerization needs to be considered. However, no report has been made to date as regards the multimerization of recombinant AIM. Furthermore, since AIM that formed a complex with IgM pentamer becomes inactive, when recombinant AIM is administered as a pharmaceutical product, it is necessary to control the formation of a complex of AIM and IgM pentamer. This problem remains unsolved.

DOCUMENT LIST

Patent Documents patent document 1: WO 2010/140531
patent document 2: WO 2013/162021
patent document 3: WO 2015/119253

Non-Patent Documents non-patent document 1: T. Miyazaki et al., J Exp Med. 189:413-422, 1999
non-patent document 2: J. Kurokawa et al., Cell Metab. 11:479-492, 2010 non-patent document 3: J. Kurokawa, Proc Natl Acad Sci USA., 108:12072-12077, 2011 non-patent document 4: S. Arai et al., Cell Rep. 3:1187-1198, 2013 non-patent document 5: T. Miyazaki et al., Cell Mol Immunol. 15:562-574, 2018

SUMMARY OF INVENTION

Technical Problem

The present invention aims to provide a recombinant AIM that maintains functions, does not multimerize, and is not inactivated by IgM.

Solution to Problem

The present inventors confirmed that a multimer is formed when a wild-type human recombinant AIM is expressed using HEK293, and focused on cysteine contained in human AIM as a cause of multimerization. The present inventors predicted from the three-dimensional structure prediction of human AIM that the cysteine at amino acid number 168 and the cysteine at amino acid number 277 of wild-type human AIM shown in SEQ ID NO: 1 are involved in the multimer formation. It was confirmed that the mutant human recombinant AIM does not multimerize when a mutant human recombinant AIM in which the cysteine is substituted with serine is prepared. The recovery efficiency of the mutant recombinant AIM increased as compared to that of the wild-type recombinant AIM. Furthermore, the mutant human recombinant AIM maintained the endocytotic activity on macrophages, which is one of the functions of wild-type human AIM. Surprisingly, it was confirmed that the activity was significantly improved in AIM in which cysteine of amino acid number 168 of wild-type human AIM shown in SEQ ID NO: 1 was replaced with serine. It was also confirmed that the wild-type mouse recombinant AIM forms a dimer, and it was also found that the cysteine at amino acid number 168 of the wild-type mouse AIM shown in SEQ ID NO: 2 is the cause of dimer formation. Furthermore, the mutant human AIM and the mutant mouse AIM in which the cysteine at amino acid number 168 of wild-type human AIM and the cysteine at amino acid number 168 of wild-type mouse AIM are respectively substituted with serine do not form a complex with the IgM pentamer. The present inventors have conducted further studies based on these findings and completed the present invention.

That is, the present invention provides

[1] a mutant human AIM comprising an amino acid sequence of any one of the following (1) to (5) and having an activity of wild-type human AIM (1) an amino acid sequence wherein cysteine at amino acid number 168 of the amino acid sequence shown in SEQ ID NO: 1 is substituted with another amino acid, (2) an amino acid sequence wherein cysteine at amino acid number 277 of the amino acid sequence shown in SEQ ID NO: 1 is substituted with another amino acid, (3) an amino acid sequence wherein cysteine at amino acid number 168 of the amino acid sequence shown in SEQ ID NO: 1 is substituted with another amino acid, and an amino acid sequence wherein cysteine at amino acid number 277 of the amino acid sequence shown in SEQ ID NO: 1 is substituted with another amino acid, (4) an amino acid sequence substantially the same as the amino acid sequence of any one of (1) to (3), and cysteines present in the amino acid sequence of any one of (1) to (3) and the substituted another amino acid remain, (5) an amino acid sequence further comprising deletion, addition, insertion or substitution of one to several amino acids or a combination thereof at a position other than cysteines present in the amino acid sequence of any one of (1) to (3) and the substituted another amino acid;

[2] the mutant human AIM of [1], wherein the another amino acid is an amino acid selected from the group consisting of asparagine, glutamine, serine, and threonine;

[3] the mutant human AIM of [1], wherein the another amino acid is serine;

[4] a mutant mouse AIM comprising an amino acid sequence of any one of the following (1) to (3) and having an activity of wild-type mouse AIM (1) an amino acid sequence wherein cysteine at amino acid number 168 of the amino acid sequence shown in SEQ ID NO: 2 is substituted with another amino acid, (2) an amino acid sequence substantially the same as the amino acid sequence of (1), and cysteines present in the amino acid sequence of (1) and the substituted another amino acid remain, (3) an amino acid sequence further comprising deletion, addition, insertion or substitution of one to several amino acids or a combination thereof at a position other than cysteines present in the amino acid sequence of (1) and the substituted another amino acid;

[5] the mutant mouse AIM of [4], wherein the another amino acid is an amino acid selected from the group consisting of asparagine, glutamine, serine, and threonine;

[6] the mutant mouse AIM of [4], wherein the another amino acid is serine;

[7] a nucleic acid comprising the base sequence of the following (1) or (2)

(1) a base sequence encoding the mutant human AIM of any one of [1] to [3], (2) a base sequence encoding the mutant mouse AIM of any one of [4] to [6];

[8] an expression vector comprising the nucleic acid of [7];

[9] a host cell comprising the expression vector of [8];

[10] a method for producing a mutant human AIM or a mutant mouse AIM, comprising culturing the host cell of [9];

[11] a pharmaceutical composition comprising a mutant AIM of the following (1) or (2)

(1) the mutant human AIM of any one of [1] to [3], (2) the mutant mouse AIM of any one of [4] to [6];

and the like.

Advantageous Effects of Invention

The mutant AIM of the present invention has the function equivalent to that of the wild-type recombinant AIM, or has an improved function, and is characterized in that it does not multimerize when expressed as a recombinant AIM. By the absence of multimerization, recombinant AIM does not precipitate by insolubilization and, as a result, the recovery rate of recombinant AIM is improved and the risk associated with in vivo administration is avoided. Furthermore, the mutant AIM of the present invention has a feature that, when administered to a living body, it does not form a complex with an IgM pentamer and, as a result, is not inactivated. Therefore, a decrease in the titer of the administered mutant AIM can be prevented and the dose can be reduced.

monomer, Dimer: dimer, Polymer: multimer. The dark-colored part at the top of the gel (indicated by an arrow) is a multimer having a huge molecular weight.

Figure 2:
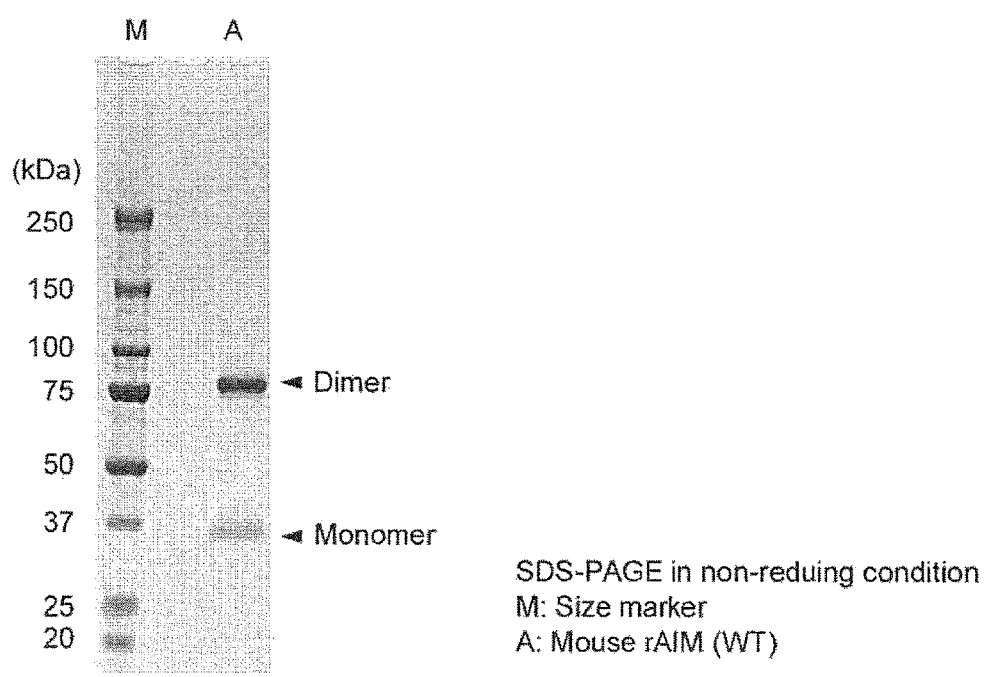

FIG. 2 shows an electrophoretic image of wild-type mouse rAIM after purification and concentration. Monomer: monomer, Dimer: dimer.

FIG. 3 shows the amino acid sequences of wild-type, 2CS, 3CS and 2/3CS human AIMs. The underlined part indicates the hinge connecting the SRCR domains.

Figure 4:
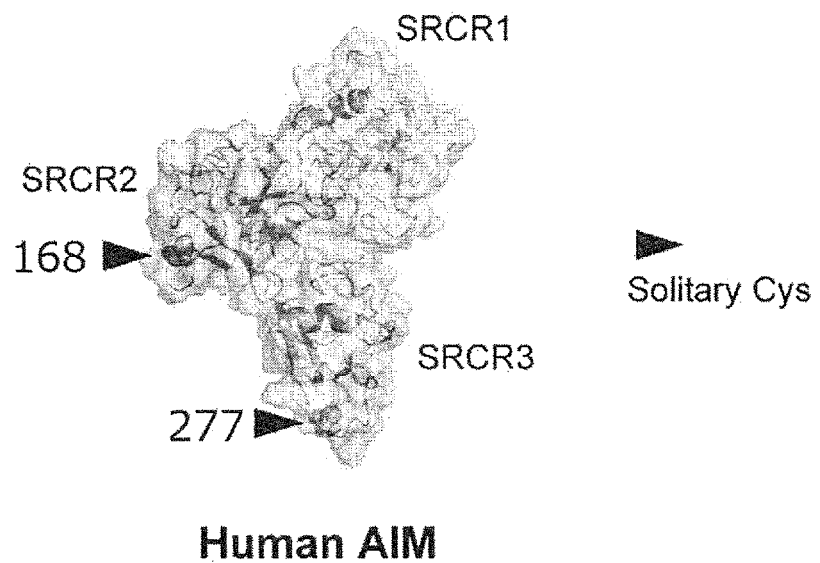

FIG. 4 shows a three-dimensional structure of wild-type human AIM.

Figure 5:
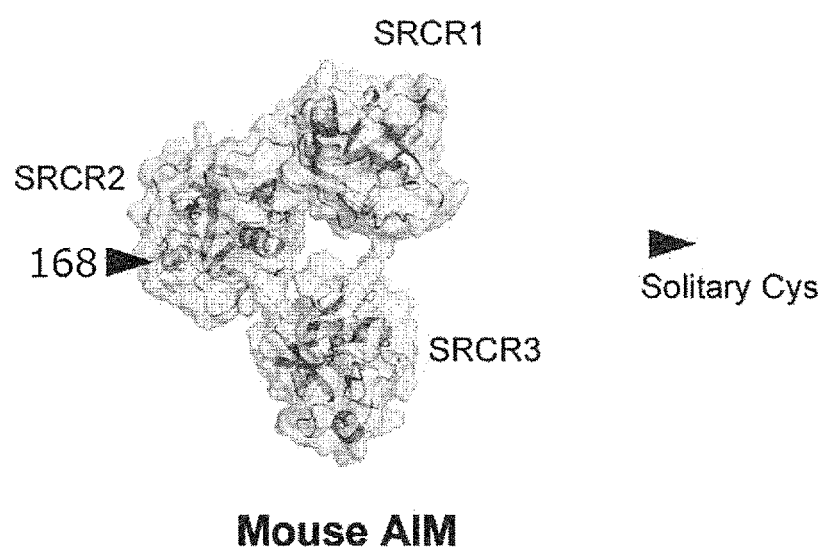

FIG. 5 shows a three-dimensional structure of wild-type mouse AIM.

FIG. 6 shows the amino acid sequences of wild-type and 2CS mouse AIMS. The underlined part indicates the hinge connecting the SRCR domains.

Figure 7:
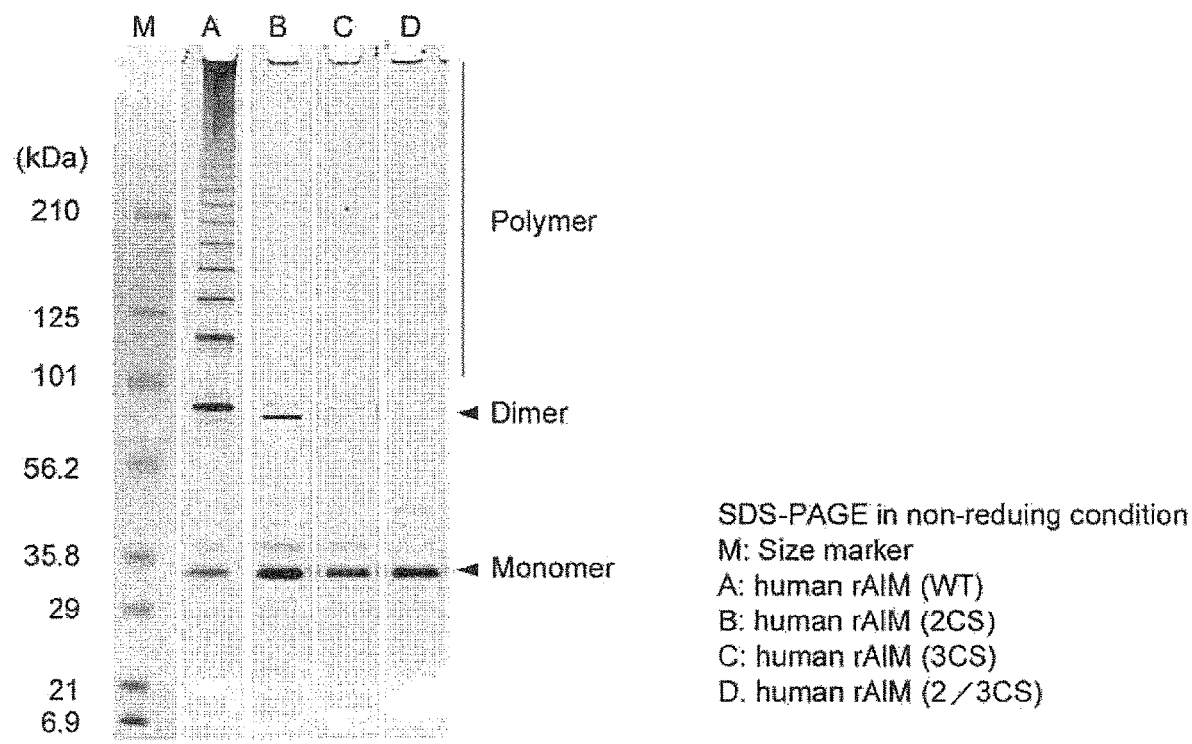

FIG. 7 shows electrophoretic images of wild-type, 2CS, 3CS and 2/3CS human rAIMs after purification and concentration. Monomer: monomer, Dimer: dimer, Polymer: multimer. The other bands are contamination with non-specific proteins other than AIM.

Figure 8:

FIG. 8 shows an electrophoretic image of wild-type and 2CS mouse rAIMs after purification and concentration. Monomer: monomer, Dimer: dimer.

Figure 9:
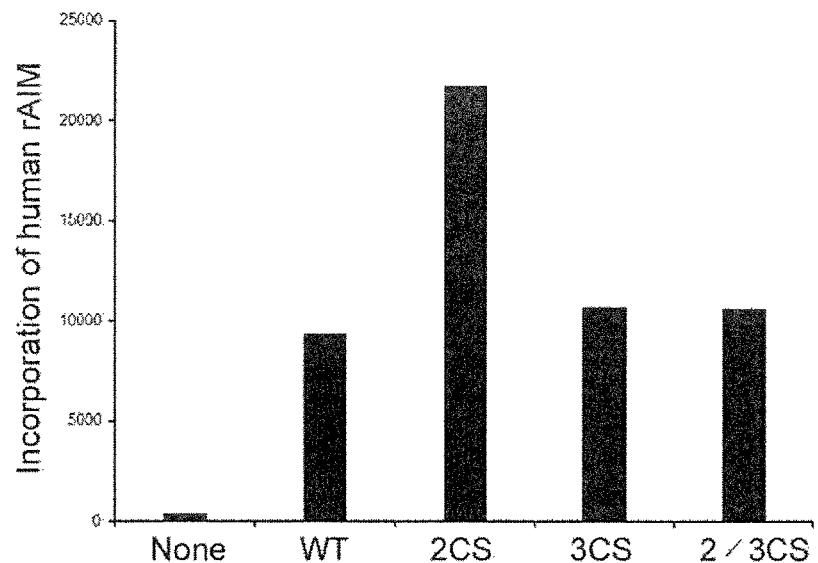

FIG. 9 is a drawing showing uptake of rAIM by peritoneal macrophage cells. The vertical axis shows fluorescence intensity.

Figure 10:
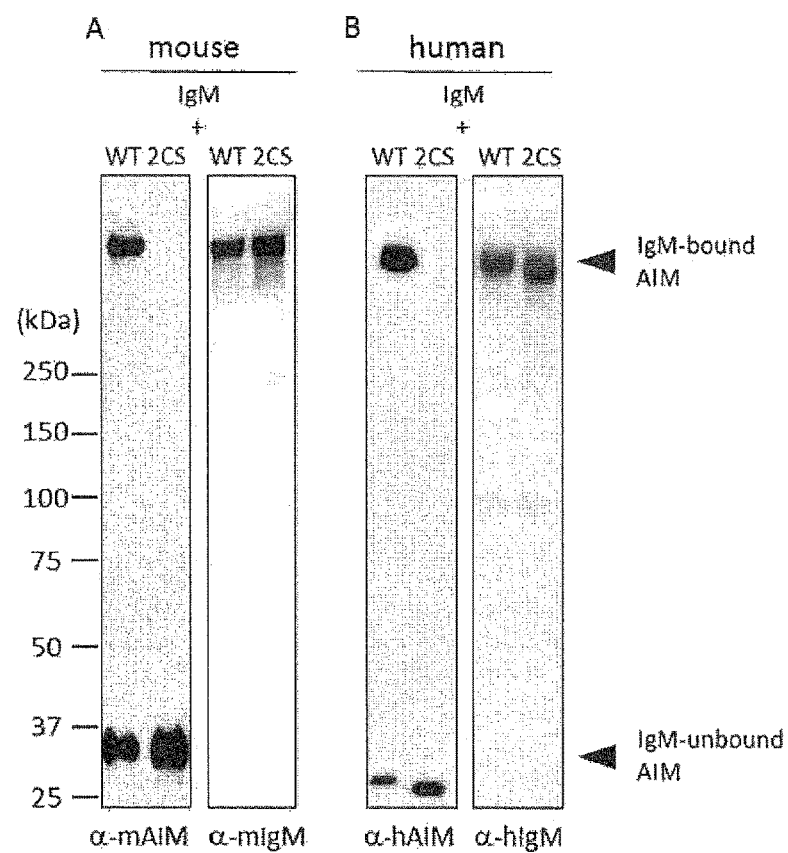

FIG. 10 shows a Western blot image (A) of proteins obtained from culture supernatant containing wild-type or 2CS mouse rAIM and mouse IgM pentamer, and a Western blot image (B) of proteins obtained from culture supernatant containing wild-type or 2CS human rAIM and human IgM pentamer. a-mAIM: anti-mouse AIM, a-hAIM: anti-human AIM, a-mIgM: anti-mouse IgM, a-hIgM: anti-human IgM.

DESCRIPTION OF EMBODIMENTS

The present invention provides a mutant human AIM comprising an amino acid sequence of any one of the following
(1a) to (5a) and having an activity of wild-type human AIM (hereinafter to be also referred to as the mutant human AIM of the present invention)
(1a) an amino acid sequence wherein cysteine at amino acid number 168 of the amino acid sequence shown in SEQ ID NO: 1 is substituted with another amino acid,
(2a) an amino acid sequence wherein cysteine at amino acid number 277 of the amino acid sequence shown in SEQ ID NO: 1 is substituted with another amino acid,
(3a) an amino acid sequence wherein cysteine at amino acid number 168 of the amino acid sequence shown in SEQ ID NO: 1 is substituted with another amino acid, and an amino acid sequence wherein cysteine at amino acid number 277 of the amino acid sequence shown in SEQ ID NO: 1 is substituted with another amino acid,
(4a) an amino acid sequence substantially the same as the amino acid sequence of any one of (1a) to (3a), and cysteines present in the amino acid sequence of any one of (1a) to (3a) and the substituted another amino acid remain,
(5a) an amino acid sequence further comprising deletion, addition, insertion or substitution of one to several amino acids or a combination thereof at a position other than cysteines present in the amino acid sequence of any one of (1a) to (3a) and the substituted another amino acid.

In addition, the mutant human AIM of the present invention preferably contains the amino acid sequence of any one of the following (1b) to (5b).

(1b) an amino acid sequence wherein cysteine at amino acid number 168 of the amino acid sequence shown in SEQ ID NO: 1 is substituted with serine (SEQ ID NO: 3),
(2b) an amino acid sequence wherein cysteine at amino acid number 277 of the amino acid sequence shown in SEQ ID NO: 1 is substituted with serine (SEQ ID NO: 4),
(3b) an amino acid sequence wherein cysteine at amino acid number 168 of the amino acid sequence shown in SEQ ID NO: 1 is substituted with serine, and an amino acid sequence wherein cysteine at amino acid number 277 of the amino acid sequence shown in SEQ ID NO: 1 is substituted with serine (SEQ ID NO: 5),
(4b) an amino acid sequence substantially the same as the amino acid sequence of any one of (1b) to (3b), and cysteines present in the amino acid sequence of any one of (1b) to (3b) and the substituted serine remain,
(5b) an amino acid sequence further comprising deletion, addition, insertion or substitution of one to several amino acids or a combination thereof at a position other than cysteines present in the amino acid sequence of any one of (1b) to (3b) and the substituted serine.

In the present invention, the amino acid sequence shown in SEQ ID NO: 1 is the amino acid sequence of wild-type human AIM. The wild-type human AIM is a protein mainly present in blood containing three cysteine-rich Scavenger-Receptor Cysteine-Rich (SRCR) domains. The SRCR1 domain, SRCR2 domain, and SRCR3 domain contained in wild-type human AIM contain 8, 9, and 9 cysteines, respectively. Of these cysteines, 8, 8, and 8 cysteines respectively contribute to formation intramolecular disulfide bond and wild-type human AIM forms a higher-order structure. The cysteines that are not involved in the formation of higher-order structure of wild-type human AIM in vivo are the cysteine at amino acid number 168 and the cysteine at amino acid number 277 in SEQ ID NO: 1. These two cysteines present in wild-type human AIM do not contribute to the intramolecular disulfide bond, but instead form an intermolecular disulfide bond between recombinant human AIMS. As a result, recombinant human AIM multimerizes and precipitates as an insolubilized protein. Furthermore, the above-mentioned cysteine at amino acid number 168 of SEQ ID NO: 1 forms a complex consisting of wild-type human AIM and human IgM pentamer by forming an intermolecular disulfide bond with a particular cysteine in the IgM pentamer and inactivates wild-type human AIM.

As mentioned above, the mutant human AIM of the present invention contains the amino acid sequence of any of the following (1a) to (3a).
(1a) an amino acid sequence wherein cysteine at amino acid number 168 of the amino acid sequence shown in SEQ ID NO: 1 is substituted with another amino acid.
(2a) an amino acid sequence wherein cysteine at amino acid number 277 of the amino acid sequence shown in SEQ ID NO: 1 is substituted with another amino acid.
(3a) an amino acid sequence wherein cysteine at amino acid number 168 of the amino acid sequence shown in SEQ ID NO: 1 is substituted with another amino acid, and an amino acid sequence wherein cysteine at amino acid number 277 of the amino acid sequence shown in SEQ ID NO: 1 is substituted with another amino acid.

The recombinant mutant human AIM of the present invention prevents formation of intermolecular disulfide bond between recombinant human AIMs by substituting cysteine at amino acid number 168 and/or cysteine at amino acid number 277 in the amino acid sequence shown in SEQ ID NO: 1 with different amino acids, whereby multimerization of recombinant human AIM can be prevented. In addition, it prevents formation of intermolecular disulfide bond between recombinant human AIM and IgM pentamer by substituting cysteine at amino acid number 168 in the amino acid sequence shown in SEQ ID NO: 1 with a different amino acid, whereby inactivation of recombinant human AIM can be prevented. The different amino acids used for substitution of the above-mentioned cysteine at amino acid number 168 and/or cysteine at amino acid number 277 in the amino acid sequence shown in SEQ ID NO: 1 is not particularly limited as long as the obtained mutant human AIM can maintain or improve the activities similar to those of the wild-type human AIM (here, "activity" means, for example, endocytosis activity to macrophages, apoptosis suppressive activity of macrophages, arteriosclerosis maintenance/promotion activity, adipocyte differentiation suppressive activity, adipocyte lipolytic activity, adipocyte reducing activity, CD36 binding activity, adipocyte endocytosis activity, FAS binding activity, FAS function suppressive activity, antiobesity activity, liver diseases (fatty liver, NASH, liver cirrhosis, liver cancer), preventive or therapeutic activity of kidney diseases (acute renal failure, chronic nephritis, chronic renal failure, nephrotic syndrome, diabetic nephropathy, nephrosclerosis, IgA nephropathy, hypertensive nephropathy, nephropathy associated with collagen disease or IgM nephropathy), and an amino acid showing similar physicochemical properties as cysteine is preferably mentioned. The different amino acids for substituting the above-mentioned cysteine at amino acid number 168 and the different amino acids for substituting cysteine at amino acid number 277 in the amino acid sequence shown in SEQ ID NO: 1 may be the same or different. Examples of the amino acid similar to cysteine include amino acids classified as polar neutral amino acids, and specifically include amino acids selected from the group consisting of asparagine, glutamine, serine, and threonine. Among these, serine is preferred from the viewpoint of structural similarity. Therefore, the mutant human AIM of the present invention containing any of the amino acid sequences of the above-mentioned (1a) to (3a) may preferably be a mutant human AIM containing any of the following amino acid sequences.

(1b) an amino acid sequence wherein cysteine at amino acid number 168 of the amino acid sequence shown in SEQ ID NO: 1 is substituted with serine (SEQ ID NO: 3).

(2b) an amino acid sequence wherein cysteine at amino acid number 277 of the amino acid sequence shown in SEQ ID NO: 1 is substituted with serine (SEQ ID NO: 4).

(3b) an amino acid sequence wherein cysteine at amino acid number 168 of the amino acid sequence shown in SEQ ID NO: 1 is substituted with serine, and an amino acid sequence wherein cysteine at amino acid number 277 of the amino acid sequence shown in SEQ ID NO: 1 is substituted with serine (SEQ ID NO: 5).

Particularly, the endocytic activity of (1b) a mutant human AIM containing the amino acid sequence (SEQ ID NO: 3) in which the cysteine at amino acid number 168 of the amino acid sequence shown in SEQ ID NO: 1 is substituted with serine is higher than the activity of wild-type human AIM as shown in the below-mentioned Examples and the function as AIM is suggested to be more superior.

The mutant human AIM of the present invention may contain the amino acid sequence of the following (4a) or (5a) in place of the amino acid sequence of any of the above-mentioned (1a) to (3a).

(4a) an amino acid sequence substantially the same as the amino acid sequence of any one of (1a) to (3a), and cysteines present in the amino acid sequence of any one of (1a) to (3a) and the substituted another amino acid remain, (5a) an amino acid sequence further comprising deletion, addition, insertion or substitution of one to several amino acids or a combination thereof at a position other than cysteines present in the amino acid sequence of any one of (1a) to (3a) and the substituted another amino acid.

The mutant human AIM of the present invention may contain the amino acid sequence of the following (4b) or (5b) in place of the amino acid sequence of any of the above-mentioned (1b) to (3b).

(4b) an amino acid sequence substantially the same as the amino acid sequence of any one of (1b) to (3b), and cysteines present in the amino acid sequence of any one of (1b) to (3b) and the substituted serine remain.

(5b) an amino acid sequence further comprising deletion, addition, insertion or substitution of one to several amino acids or a combination thereof at a position other than cysteines present in the amino acid sequence of any one of (1b) to (3b) and the substituted serine.

Specific examples of the amino acid sequence substantially the same as the above-mentioned amino acid sequence of any one of (1a) to (3a) (or any one of the above-mentioned (1b) to (3b)), in which cysteines present in the amino acid sequence of any one of the above-mentioned (1a) to (3a) (or the above-mentioned (1b) to (3b)) and the substituted another amino acid (preferably, the substituted another amino acid is serine) remain include an amino acid in which cysteines at amino acid numbers 10, 26, 39, 44, 73, 83, 91, 101, 124, 140, 153, 158, 168, 185, 195, 205, 215, 230, 246, 259, 264, 277, 292, 302, 312 and 322 of the amino acid sequence of any one of the above-mentioned (1a) to (3a) (or any one of the above-mentioned (1b) to (3b)), and the substituted another amino acids (preferably, the substituted another amino acid is serine) are not changed, and the amino acid sequence parts other than the amino acids have a homology of not less than about 85%, preferably not less than about 90%, further preferably not less than about 95%, most preferably not less than about 98%, with the amino acid sequence shown in SEQ ID NO: 1 and the like. As used herein, the "homology" means the proportion (%) of the same amino acid residues and similar amino acid residues relative to the total overlapping amino acid residues, in an optimal alignment (preferably, the algorithm is capable of considering introduction of gap into one of or both of the sequences for optimal alignment), when two amino acid sequences are aligned using a mathematical algorithm known in the technical field. The "similar amino acid" means amino acids having similar physicochemical properties and, for example, amino acids classified in the same group such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having a hydroxyl group (Ser, Thr), amino acids having a small side chain (Gly, Ala, Ser, Thr, Met) and the like can be mentioned. It is predicted that the substitution with such similar amino acids does not change the phenotype of the protein (that is, conservative amino acid substitution). Specific examples of the conservative amino acid substitution are well known in the technical field and are described in various documents (e.g., Bowie et al., Science, 247: 1306-1310 (1990)).

The homology of the amino acid sequences in the present specification can be calculated using homology calculation algorithm NCBI BLAST (National Center for Biotechnology Information Basic Local Alignment Search Tool) and under the following conditions (expectancy=10; gap allowed; matrix=BLOSUM62; filtering=OFF). Examples of other algorithm for determining the homology of the amino acid sequence include the algorithm described in Karlin et al., Proc. Natl. Acad. Sci. USA, 90: 5873-5877 (1993) [said algorithm is incorporated in the NBLAST and XBLAST program (version 2.0) (Altschul et al., Nucleic Acids Res., 25: 3389-3402 (1997))], the algorithm described in Needleman et al., J. Mol. Biol., 48: 444-453 (1970) [said algorithm is incorporated in the GAP program in the GCG software package], the algorithm described in Myers and Miller, CABIOS, 4: 11-17 (1988) [said algorithm is incorporated in ALIGN program (version 2.0) which is a part of the CGC sequence alignment software package], the algorithm described in Pearson et al., Proc. Natl. Acad. Sci. USA, 85: 2444-2448 (1988) [said algorithm is incorporated in the FASTA program in the GCG software package] and the like, and these can also be similarly used preferably.

More preferably, examples of the amino acid sequence substantially the same as the above-mentioned amino acid sequence of any one of (1a) to (3a) (or any one of the above-mentioned (1b) to (3b)), in which cysteines present in the amino acid sequence of any one of the above-mentioned (1a) to (3a) (or the above-mentioned (1b) to (3b)) and the substituted another amino acid (preferably, the substituted another amino acid is serine) remain include an amino acid which cysteines at amino acid numbers 10, 26, 39, 44, 73, 83, 91, 101, 124, 140, 153, 158, 168, 185, 195, 205, 215, 230, 246, 259, 264, 277, 292, 302, 312 and 322 of the amino acid sequence of any one of the above-mentioned (1a) to (3a) (or any one of the above-mentioned (1b) to (3b)), and the substituted another amino acids (preferably, the substituted another amino acid is serine) are not changed, and the amino acid sequence parts other than the amino acids have an identity of not less than about 85%, preferably not less than about 90%, further preferably not less than about 95%, most preferably not less than about 98%, with the amino acid sequence shown in SEQ ID NO: 1.

The position other than cysteines present in the amino acid sequence of any one of the above-mentioned (1a) to (3a) (or the above-mentioned (1b) to (3b)) and the substituted another amino acid (preferably, the substituted another amino acid is serine) is the position other than the amino acid numbers 10, 26, 39, 44, 73, 83, 91, 101, 124, 140, 153, 158, 168, 185, 195, 205, 215, 230, 246, 259, 264, 277, 292, 302, 312 and 322 of the amino acid sequence of any one of the above-mentioned (1a) to (3a) (or any one of the above-mentioned (1b) to (3b)), and is not particularly limited as long as it is a position at which a mutant human AIM containing deletion, addition, insertion or substitution, or a combination thereof can maintain or improve the activities the wild-type human AIM has. The number of deletion, addition, insertion or substitution, or a combination thereof is one to several, preferably, 1 to 5, 1 to 4, 1 to 3, or 1 or 2. The amino acids to be used for substitution may be similar to the above-mentioned amino acids.

The present invention also provides a mutant mouse AIM containing an amino acid sequence of any one of the following (1c) to (3c) and having an activity of wild-type mouse AIM (hereinafter to be also referred to as the mutant mouse AIM of the present invention)
(1c) an amino acid sequence wherein cysteine at amino acid number 168 of the amino acid sequence shown in SEQ ID NO: 2 is substituted with another amino acid,
(2c) an amino acid sequence substantially the same as the amino acid sequence of (1c), and cysteines present in the amino acid sequence of (1c) and the substituted another amino acid remain,
(3c) an amino acid sequence further comprising deletion, addition, insertion or substitution of one to several amino acids or a combination thereof at a position other than cysteines present in the amino acid sequence of (1c) and the substituted amino acid.

In addition, the mutant mouse AIM of the present invention preferably contains the amino acid sequence of any one of the following (1d) to (3d).
(1d) an amino acid sequence wherein cysteine at amino acid number 168 of the amino acid sequence shown in SEQ ID NO: 2 is substituted with serine (SEQ ID NO: 6),
(2d) an amino acid sequence substantially the same as the amino acid sequence of (1d), and cysteines present in the amino acid sequence of (1d) and the substituted serine remain,
(3d) an amino acid sequence further comprising deletion, addition, insertion or substitution of one to several amino acids or a combination thereof at a position other than cysteines present in the amino acid sequence of (1d) and the substituted serine.

In the present invention, the amino acid sequence shown in SEQ ID NO: 2 shows the amino acid sequence of wild-type mouse AIM. Similar to the wild-type human AIM, the wild-type mouse AIM contains 3 SRCR domains. Cysteines contained in the SRCR1 domain, SRCR2 domain and SRCR3 domain are, unlike wild-type human AIM, 8, 9 and 8, respectively. The cysteine that is not involved in the formation of higher-order structure of wild-type mouse AIM in vivo is only the cysteine at amino acid number 168 in SEQ ID NO: 2. This cysteine present in wild-type mouse AIM does not contribute to the intramolecular disulfide bond, but instead forms an intermolecular disulfide bond between recombinant mouse AIMs. As a result, recombinant mouse AIM dimerizes. Furthermore, the above-mentioned cysteine at amino acid number 168 of SEQ ID NO: 2 forms a complex consisting of wild-type mouse AIM and mouse IgM pentamer by forming an intermolecular disulfide bond with a particular cysteine in the IgM pentamer and inactivates wild-type mouse AIM.

As mentioned above, the mutant mouse AIM of the present invention contains (1c) amino acid sequence wherein cysteine at amino acid number 168 of the amino acid sequence shown in SEQ ID NO: 2 is substituted with another amino acid.

The mutant mouse AIM of the present invention prevents formation of intermolecular disulfide bond between recombinant mouse AIMs by substituting cysteine at amino acid number 168 in the amino acid sequence shown in SEQ ID NO: 2 with a different amino acid, whereby dimerization of recombinant mouse AIM can be prevented. In addition, it prevents formation of intermolecular disulfide bond between recombinant mouse AIM and IgM pentamer by substituting cysteine at amino acid number 168 in the amino acid sequence shown in SEQ ID NO: 2 with a different amino acid, whereby inactivation of recombinant mouse AIM can be prevented. The different amino acids used for substitution of the above-mentioned cysteine at amino acid number 168 in the amino acid sequence shown in SEQ ID NO: 2 is not particularly limited as long as the obtained mutant mouse AIM can maintain or improve the activities similar to those of the wild-type mouse AIM (here, "activity" means the same as in wild-type human AIM). An amino acid showing physicochemical properties similar to those of cysteine is preferred. Examples of the amino acid similar to cysteine include amino acids classified as polar neutral amino acids, and specifically include amino acids selected from the group consisting of asparagine, glutamine, serine, and threonine.

Among these, serine is preferred from the viewpoint of structural similarity. Therefore, the above-mentioned mutant mouse AIM of the present invention is preferably mutant mouse AIM containing (1d) an amino acid sequence wherein cysteine at amino acid number 168 of the amino acid sequence shown in SEQ ID NO: 2 is substituted with serine (SEQ ID NO: 6).

The mutant mouse AIM of the present invention may contain the amino acid sequence of the following (2c) or (3c) in place of the amino acid sequence of the above-mentioned (1c).

(2c) an amino acid sequence substantially the same as the amino acid sequence of (1c), and cysteines present in the amino acid sequence of (1c) and the substituted another amino acid remain, (3c) an amino acid sequence further comprising deletion, addition, insertion or substitution of one to several amino acids or a combination thereof at a position other than cysteines present in the amino acid sequence of (1c) and the substituted amino acid.

The mutant mouse AIM of the present invention may also contain the amino acid sequence of the following (2d) or (3d) in place of the amino acid sequence of the above-mentioned (1d).

(2d) an amino acid sequence substantially the same as the amino acid sequence of (1d), and cysteines present in the amino acid sequence of (1d) and the substituted serine remain, (3d) an amino acid sequence further comprising deletion, addition, insertion or substitution of one to several amino acids or a combination thereof at a position other than cysteines present in the amino acid sequence of (1d) and the substituted serine.

Specific examples of the amino acid sequence substantially the same as the above-mentioned amino acid sequence of (1c) (or the above-mentioned (1d)), in which cysteines present in the amino acid sequence of the above-mentioned (1c) (or the above-mentioned (1d)) and the substituted another amino acid (preferably, the substituted another amino acid is serine) remain include an amino acid in which cysteines at amino acid numbers 10, 26, 39, 44, 72, 82, 91, 101, 124, 140, 153, 158, 168, 185, 195, 204, 214, 229, 245, 258, 263, 291, 301, 311 and 321 of the amino acid sequence of the above-mentioned (1c) (or the above-mentioned (1d)), and the substituted another amino acids (preferably, the substituted another amino acid is serine) are not changed, and the amino acid sequence parts other than the amino acids have a homology of not less than about 85%, preferably not less than about 90%, further preferably not less than about 95%, most preferably not less than about 98%, with the amino acid sequence shown in SEQ ID NO: 2 and the like. As used herein, the "homology" means the same as above.

More preferably, the amino acid sequence substantially the same as the above-mentioned amino acid sequence of (1c) (or the above-mentioned (1d)), in which cysteines present in the amino acid sequence of the above-mentioned (1c) (or the above-mentioned (1d)) and the substituted another amino acid (preferably, the substituted another amino acid is serine) remain is an amino acid in which cysteines at amino acid numbers 10, 26, 39, 44, 72, 82, 91, 101, 124, 140, 153, 158, 168, 185, 195, 204, 214, 229, 245, 258, 263, 291, 301, 311 and 321 of the amino acid sequence of the above-mentioned (1c) (or the above-mentioned (1d)), and the substituted another amino acids (preferably, the substituted another amino acid is serine) are not changed, and the amino acid sequence parts other than the amino acids have an identity of not less than about 85%, preferably not less than about 90%, further preferably not less than about 95%, most preferably not less than about 98%, with the amino acid sequence shown in SEQ ID NO: 2 and the like.

The position other than cysteines present in the amino acid sequence of the above-mentioned (1c) (or the above-mentioned (1d)) and the substituted another amino acid (preferably, the substituted another amino acid is serine) is the position other than the amino acid numbers 10, 26, 39, 44, 72, 82, 91, 101, 124, 140, 153, 158, 168, 185, 195, 204, 214, 229, 245, 258, 263, 291, 301, 311 and 321 of the amino acid sequence of the above-mentioned (1c) (or the above-mentioned (1d)), and is not particularly limited as long as it is a position at which a mutant mouse AIM containing deletion, addition, insertion or substitution, or a combination thereof can maintain or improve the activities the wild-type mouse AIM has. The activities of wild-type mouse AIM, amino acid used for substitution, number amino acids for deletion, addition, insertion or substitution or a combination thereof, and the like may be similar to those of the mutant human AIM of the present invention.

The mutant human AIM of the present invention and mutant mouse AIM (hereinafter the mutant human AIM of the present invention and mutant mouse AIM are also collectively referred to as the mutant AIM of the present invention) may be further added with a signal peptide. The wild-type human AIM is translated in the cell as an immature wild-type human AIM in which a signal peptide shown in SEQ ID NO: 7 is linked to the N-terminal of the amino acid sequence shown in SEQ ID NO: 1, and converted to a mature protein by cleavage of the aforementioned signal peptide when secreted outside the cell. Similarly, wild-type mouse AIM is translated in the cell as an immature wild-type mouse AIM in which a signal peptide shown in SEQ ID NO: 8 is linked to the N-terminal of the amino acid sequence shown in SEQ ID NO: 2, and converted to a mature protein by cleavage of the aforementioned signal peptide when secreted outside the cell. Due to the addition of the signal peptide, when mutant AIM is expressed in the cells as a recombinant AIM, the mutant AIM is secreted outside the cell and the recovery is facilitated.

The mutant AIM of the present invention can be produced according to a known peptide synthesis method.

The peptide synthesis method may be any of, for example, solid phase synthesis process and solution phase synthesis process. The object mutant AIM can be produced by condensing a partial peptide or amino acid capable of constituting the mutant AIM of the present invention and the remaining portion and, when the resultant product has a protecting group, removing the protecting group.

Here, the condensation and removal of the protecting group are performed according to a method known per se, for example, the methods described in the following (1) and (2).

(1) M. Bodanszky and M. A. Ondetti, Peptide Synthesis, Interscience Publishers, New York (1966)

(2) Schroeder and Luebke, The Peptide, Academic Press, New York (1965)

The thus-obtained mutant AIM of the present invention can be purified and isolated by a known purification method. Examples of the purification method here include solvent extraction, distillation, column chromatography, liquid chromatography, recrystallization, a combination of these and the like.

When the mutant AIM of the present invention obtained by the above-mentioned method is a free form, the free form can be converted to a suitable salt by a known method or a method analogous thereto. Conversely, when the mutant AIM of the present invention is obtained as a salt, the salt can be converted to a free form or other salt by a known method or a method analogous thereto.

Furthermore, the mutant AIM of the present invention can also be produced by culturing a host cell containing an expression vector containing a nucleic acid encoding same, and separating and purifying the mutant AIM from the resulting culture. The nucleic acid encoding the mutant AIM of the present invention may be DNA or RNA, or may be DNA/RNA chimera. Preferred is DNA. In addition, the nucleic acid may be double stranded or single stranded. When it is double stranded, it may be a double stranded DNA, a double stranded RNA or a DNA:RNA hybrid. When it is single stranded, it may be a sense strand (i.e., coding strand), or an antisense strand (i.e., non-coding strand).

As DNA encoding the mutant AIM of the present invention, synthetic DNA and the like can be mentioned. For example, it can be acquired by converting, according to a method known per se such as ODA-LA PCR method, Gapped duplex method, Kunkel method and the like, or a method analogous thereto, and by using a known kit, for example, Mutan™-super Express Km (TAKARA BIO INC.), Mutan™-K (TAKARA BIO INC.) and the like, a primer for mutation introduction, and a full-length AIM cDNA (e.g., in the case of human, the base sequence shown in SEQ ID NO: 9 can be mentioned, in the case of mouse, the base sequence shown in SEQ ID NO: 10 can be mentioned), which was directly amplified by Reverse Transcriptase-PCR (hereinafter abbreviated as "RT-PCR method") by using total RNA or mRNA fraction prepared from a cell or tissue as a template. Alternatively, it can also be acquired by converting, according to the above-mentioned method, a cDNA cloned from a cDNA library, prepared by inserting a fragment of the above-mentioned total RNA or mRNA into a suitable vector, by colony or plaque hybridization method or PCR method and the like. The vector used for the library may be any such as bacteriophage, plasmid, cosmid, phagemid and the like.

The nucleic acid containing a base sequence encoding the mutant AIM of the present invention is not limited as long as it is a nucleic acid containing a codon corresponding to the amino acid sequence of the mutant AIM of the present invention. Examples thereof in the case of a mutant human AIM to which a signal peptide is added include a DNA containing the same or substantially the same base sequence as the base sequence shown in SEQ ID NO: 11 in which G at base number 572 of the base sequence shown in SEQ ID NO: 9 is substituted with C, the base sequence shown in SEQ ID NO: 12 in which G at base number 899 of the base sequence shown in SEQ ID NO: 9 is substituted with C, or the base sequence shown in SEQ ID NO: 13 having both substitutions and the like, in the case of mutant mouse AIM added with signal peptide, it includes a DNA containing a base sequence the same or substantially the same as the base sequence shown in SEQ ID NO: 14 in which G at base number 581 of the base sequence shown in SEQ ID NO: 10 is substituted with C and the like.

Here, the "substantially the same base sequence" refers to a base sequence having a mutation that does not change the amino acid sequence encoded by the original base sequence (silent mutation).

An expression vector containing a nucleic acid encoding the mutant AIM of the present invention can be produced, for example, by isolating a DNA fragment encoding the aforementioned mutant AIM, and ligating the DNA fragment at the downstream of a promoter in a suitable expression vector. For example, an expression vector containing a DNA encoding the mutant human AIM of the present invention can be obtained by inserting the DNA consisting of the base sequence shown in SEQ ID NO: 11 into an expression vector pCAGGS, and transforming *Escherichia coli* with the obtained plasmid.

As the expression vector, an animal cell expressing plasmid (e.g., pCAGGS, pSRα, pA1-11, pXT1, pRc/CMV, pRc/RSV, pcDNAI/Neo) is used.

The promoter may be any as long as it is an appropriate promoter for the host used for gene expression.

For example, when the host is an animal cell, β-actin promoter, SRα promoter, SV40 promoter, LTR promoter, CMV (cytomegalovirus) promoter, RSV (Rous sarcoma virus) promoter, MoMuLV (Moloney murine leukemia virus) LTR, HSV-TK (herpes simplex virus thymidine kinase) promoter, trc promoter, trc modified promoter and the like are used.

As the expression vector, one containing, when desired, enhancer, splicing signal, poly A addition signal, selection marker, SV40 replication origin (hereinafter sometimes to be abbreviated as SV40 ori) and the like can be used besides those mentioned above. Examples of the selection marker include dihydrofolate reductase gene (hereinafter sometimes to be abbreviated as dhfr, methotrexate (MTX) resistance), neomycin resistance gene (hereinafter sometimes to be abbreviated as neo$^r$, G418 resistance) and the like. Particularly, when dhfr gene deficient Chinese hamster cell is used, and dhfr gene is used as a selection marker, the object gene can also be selected in a medium free of thymidine.

The mutant AIM can be produced by introducing an expression vector containing the above-mentioned nucleic acid encoding the mutant AIM into a host cell, and culturing the obtained host cell.

As the host cell, an animal cell is preferable for the mutant AIM of the present invention.

As the animal cell, for example, cells such as COS-7, Vero, CHO, CHO (dhfr), CHO-K1, CHO-S, L, AtT-20, GH3, FL, HEK293, NIH3T3, Balb3T3, FM3A, L929, SP2/0, P3U1, B16, P388 and the like are used.

Gene transfer can be performed according to a known method.

Gene can be introduced into the animal cell according to the method described in, for example, Cell Engineering, extra issue 8, New Cell Engineering Experimental Protocol, 263-267 (1995) (published by Shujunsha), Virology, vol. 52, 456 (1973).

A transfected host cell can be cultured according to a known method.

When the host cell is an animal cell, the medium used for culture is preferably minimum essential medium (MEM), Dulbecco's modified Eagle medium (DMEM), RPMI 1640 medium, 199 medium or the like, each containing about 5-about 20% of fetal bovine serum. The pH of the medium is preferably about 6-about 8. The transformant is cultured generally at about 30-about 40° C. for about 15-about 60 hr. Where necessary, aeration and stirring may be performed.

As mentioned above, the mutant AIM of the present invention can be produced intracellularly or extracellularly using the host cell.

The mutant AIM of the present invention can be separated and purified by a method known per se from the culture obtained by culturing the aforementioned transfected host cell.

For example, when the mutant AIM of the present invention is extracted from cytoplasm of the host cell, a method including suspending the host cells collected from a culture by a known method in a suitable buffer, rupturing the host cells by ultrasonication, lysozyme and/or freeze-thawing and the like, and obtaining a crude extract of a soluble protein by centrifugation, filtration and the like as appropriate. The buffer may contain protein denaturant such as urea, hydrochloric acid guanidine and the like, and surfactant such as TritonX-100™ and the like. When the mutant AIM of the present invention is secreted out from the cell, a method for separating the culture supernatant from the culture by centrifugation, filtration and the like, and the like is used.

The mutant AIM of the present invention contained in the thus-obtained soluble fraction and culture supernatant can be isolated and purified by a method known per se. As such method, a method utilizing the solubility such as salting out, solvent precipitation and the like; a method mainly utilizing difference in the molecular weight such as dialysis, ultrafiltration, gel filtration method, and SDS-polyacrylamide gel electrophoresis and the like; a method utilizing difference in the electric charge such as ion exchange chromatography and the like; a method utilizing specific affinity such as affinity chromatography and the like; a method utilizing difference in the hydrophobicity such as reversed-phase high performance liquid chromatography and the like; a method utilizing difference in isoelectric point such as isoelectric focusing and the like; a method using an antibody, and the like are used. These methods can also be combined as appropriate.

The presence of the thus-obtained mutant AIM of the present invention can be confirmed by enzyme immunoassay, Western blotting and the like, using an antibody to the mutant AIM.

The present invention also provides a pharmaceutical composition containing the mutant AIM of the present invention (hereinafter to be also referred to as the pharmaceutical composition of the present invention). The inventions heretofore reported that AIM can be used for the prophylaxis or treatment of obesity, hepatic diseases, and renal diseases (WO 2010/140531, WO 2013/162021, WO 2015/119253). The mutant AIM of the present invention also maintains or improves the activities similar to those of wild-type AIM, it can also be used for the prophylaxis or treatment of obesity, hepatic diseases, and renal diseases.

Examples of the subject of administration of the pharmaceutical composition of the present invention include humans and other warm-blooded animals (e.g., mouse, rat, rabbit, sheep, swine, bovine, cat, dog, monkey, avian and the like).

The hepatic diseases to be the application target of the pharmaceutical composition of the present invention include, for example, fatty liver, non-alcoholic steatohepatitis (NASH), cirrhosis, and liver cancer. The renal diseases to be the application target of the pharmaceutical composition of the present invention include, for example, acute renal failure, chronic nephritis, chronic renal failure, nephrotic syndrome, diabetic nephropathy, nephrosclerosis, IgA nephropathy, hypertensive nephropathy, and nephropathy associated with collagen disease or IgM nephropathy, and acute renal failure or chronic renal failure is preferred. The nephropathy associated with collagen disease is represented by, for example, lupus nephritis.

The pharmaceutical composition of the present invention is of low toxicity, and can be administered as a liquid as it is, or as an appropriate dosage form of pharmaceutical composition, to humans or other warm-blooded mammals (e.g., mouse, rat, rabbit, sheep, swine, bovine, cat, dog, monkey, avian and the like) orally or parenterally (e.g., intravascular administration, subcutaneous administration and the like).

As examples of the pharmaceutical composition for parenteral administration, injections, suppositories and the like are used; the injections may include dosage forms such as intravenous injections, subcutaneous injections, intracutaneous injections, intramuscular injections and drip infusion injections. Such an injection can be prepared according to a publicly known method. An injection can be prepared by, for example, dissolving, suspending or emulsifying the above-mentioned mutant human AIM of the present invention in a sterile aqueous or oily solution in common use for injections. As examples of aqueous solutions for injection, physiological saline, an isotonic solution comprising glucose or another auxiliary drug, and the like can be used, which may be used in combination with an appropriate solubilizer, for example, alcohol (e.g., ethanol), polyalcohol (e.g., propylene glycol, polyethylene glycol), non-ionic surfactant [e.g., polysorbate 80, HCO-50 (polyoxyethylene (50 mol) adduct of hydrogenated castor oil)] and the like. As examples of oily solutions, sesame oil, soybean oil and the like can be used, which may be used in combination with benzyl benzoate, benzyl alcohol and the like as solubilizers. The prepared injection solution is preferably filled in an appropriate ampoule. Suppositories used for rectal administration may be prepared by mixing the above-mentioned mutant AIM with an ordinary suppository base.

As the pharmaceutical composition for oral administration, solid or liquid dosage forms, specifically tablets (including sugar-coated tables and film-coated tablets), pills, granules, powders, capsules (including soft capsules), syrups, emulsions, suspensions and the like can be mentioned. Such a pharmaceutical composition is produced by a publicly known method, and may comprise a carrier, diluent or excipient in common use in the field of pharmaceutical making. As examples of the carrier or excipient for tablets, lactose, starch, sucrose, magnesium stearate and the like can be used.

While the dose of the pharmaceutical composition of the present invention varies depending on the subject of administration, target disease, symptoms, administration route and the like, for example, when used for an adult, the mutant AIM of the present invention is conveniently administered by intravenous injection at typically about 0.01-20 mg/kg body weight, preferably about 0.1-10 mg/kg body weight, further preferably about 0.1-5 mg/kg body weight, as one dose, about 1-5 times/day, preferably about 1-3 times/day, for about 1-21 days, preferably about 1-14 days. In the case of other parenteral administrations and oral administrations, doses similar thereto can be administered. When the symptoms are particularly severe, the dose may be increased according to the symptoms.

The pharmaceutical composition of the present invention may contain any other active ingredients that do not produce an unwanted interaction when formulated with the mutant AIM of the present invention.

EXAMPLE

The present invention is explained more specifically in the following by referring to Examples and Reference Examples, which are not to be construed as limitative.

Example 1: Formation of Wild-Type Human Recombinant AIM (rAIM) Multimer

The wild-type human rAIM was prepared as follows. That is, human AIM stable expression strain obtained by introducing pCAGGS-human AIM expression vector into HEK293 was cultured in Dulbecco's Modified Eagle Medium (DMEM, Invitrogen) containing 5% FBS, Glutamax, gentamicin for 3 days, and the culture supernatant was recovered. The recovered culture supernatant was applied to an antibody column obtained by immobilizing mouse anti-human AIM monoclonal antibody (clone 7, autologously manufactured) on HiTrap NHS-activated HP column (GE Healthcare Life Sciences) to purify human rAIM. The human rAIM bound to the antibody column was eluted with 0.1 M glycine-HCl (pH2.5), and immediately neutralized with 1 M Tris-HCl (pH 8.5) to obtain human rAIM eluate. The buffer in the eluate was substituted with Dulbecco's Phosphate-Buffered Saline (DPBS) by using Amicon Ultra filter concentrators (Millipore) to perform concentration. The protein level of the human rAIM concentrate was quantified using Bcinchoninic acid (BCA) assay (Pierce), and the final concentration was adjusted to 2.0 mg/mL with DPBS. The wild-type human rAIM protein (1 μg) purified and concentrated as mentioned above was separated under non-reducing conditions by polyacrylamide gel electrophoresis (SDS-PAGE) based on the difference in the molecular weights, Coomassie Brilliant Blue (CBB) staining was performed, and wild-type human rAIM was detected.

Figure 1:
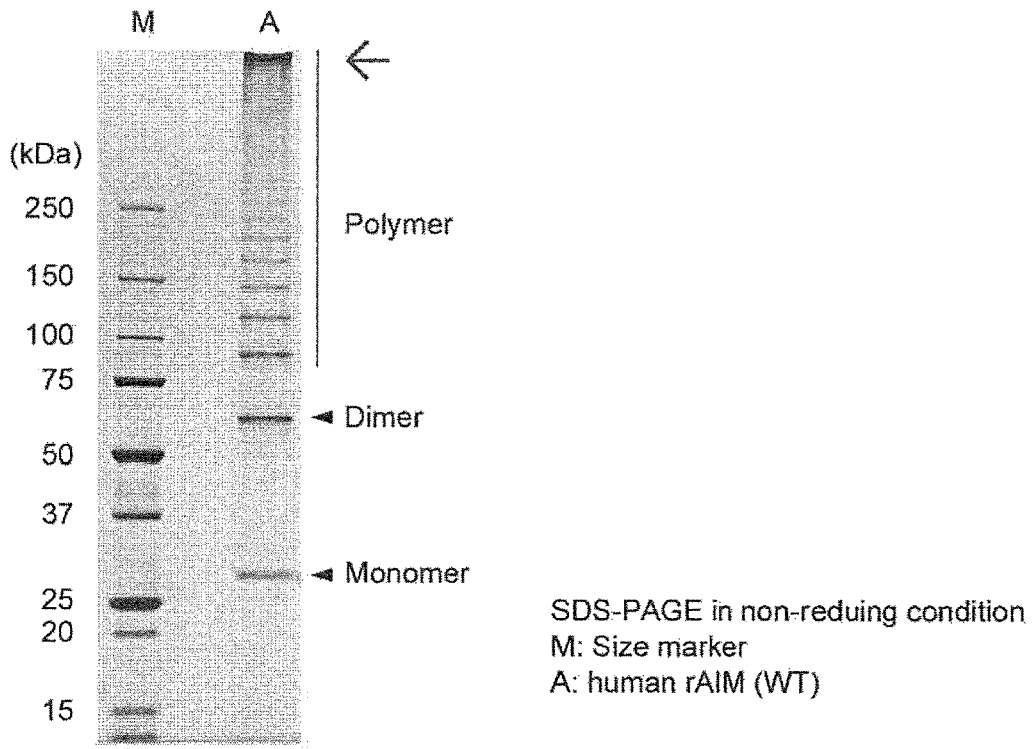
FIG. 1 shows an electrophoretic image of wild-type human rAIM after purification and concentration. Monomer.

As a result, when human rAIM was purified from the human AIM stable expression strain and prepared as a high concentration solution, human rAIM formed a multimer (FIG. 1). Particularly, precipitation of some of the multimers having a large molecular weight (complex in which a large amount of rAIM is multimerized: multimeric rAIM corresponding to the high molecular weight band in lane A of FIG. 1 and a multimeric rAIM remaining in the slot) was feared. This suggests a risk that, when human rAIM is purified and administered to a living body as a therapeutic drug, the precipitated multimers may block fine blood vessels and lead to a serious accident. In view of the possible clinical application of human rAIM in the future, creation of a mutant human AIM that does not form at least a multimer having a large molecular weight is desired.

Example 2: Formation of Wild-Type Mouse Recombinant AIM (rAIM) Multimer

The wild-type mouse rAIM was prepared as follows. That is, mouse AIM stable expression strain obtained by introducing pCAGGS-mouse AIM expression vector into HEK293 was cultured in DMEM containing 5% FBS, Glutamax, gentamicin for 3 days, and the culture supernatant was recovered. The recovered culture supernatant was applied to an antibody column obtained by immobilizing rat anti-mouse AIM monoclonal antibody (clone 36, autologously manufactured) on HiTrap NHS-activated HP column to purify mouse rAIM. The mouse rAIM bound to the antibody column was eluted with 0.1 M glycine-HCl (pH2.3), and immediately neutralized with 1 M Tris-HCl (pH 8.5) to obtain mouse rAIM eluate. The buffer in the eluate was substituted with DPBS by using Amicon Ultra filter concentrators to perform concentration. The protein level of the mouse rAIM concentrate was quantified using BCA assay, and the final concentration was adjusted to 2.0 mg/mL with DPBS. The wild-type mouse rAIM protein (1 μg) purified and concentrated as mentioned above was separated under non-reducing conditions by SDS-PAGE based on the difference in the molecular weights, CBB staining was performed, and wild-type mouse rAIM was detected.

As a result, mouse rAIM did not form a multimer like human rAIM, and monomers and dimers alone were present (FIG. 2).

Example 3: Prediction of Three-Dimensional Structure of Wild-Type Human and Mouse AIMs The wild-type human AIM has 8, 9, 9 cysteines in three SRCR domains (SRCR1, SRCR2, SRCR3), respectively (FIG. 3). A signal peptide is linked to the N-terminal of immature AIM and the immature AIM is converted to a mature protein by cleavage of the signal peptide when secreted outside the cell. To verify the possibility of the above-mentioned disulfide bond due to cysteine present in human AIM being involved in multimerization, the present inventors predicted the three-dimensional structure of human AIM. The three-dimensional structure of human AIM was predicted by two-step modeling of the partial structure shown by three SRCR domains and the entire structure including the three SRCR domains and the hinge (underlined in FIG. 3). A Swiss-Model server (swissmodel.expasy-.org/SWISS-MODEL) was used for homology modeling for each SRCR domain. As a result of individual sequence homology search by Blast and HHBlits on the three SRCR domains of human AIM, human CD6 (5a2e.1.A; PDB ID: 5A2E) which belongs to SRCR superfamily Group B to which human AIM belongs similarly showed good sequence homology of not less than 30% to all SRCR domains. Therefore, using human CD6 as a template, three-dimensional structures of three SRCR domains were constructed by Promod-II6. Next, using Prime version 4.2 (Schrodinger, LLC, New York, N.Y., 2015), the entire structure of human AIM was constructed by introducing a sequence (hinge) other than the SRCR domain. The three-dimensional structure of the entire human AIM was obtained using the molecular dynamics calculation (310 K, 20 ns) by Desmond with OPLS_2005 as a force field, and equilibrating the entire structure of the human AIM in a periodic box model filled with water molecules (SPC). The four disulfide bonds in each SRCR domain of human AIM were reproduced using the SRCR domain of human CD6 as a template. The results of prediction of the three-dimensional structure of wild-type human AIM are shown in FIG. 4. It was found that 8 cysteines of the 8, 9, 9 cysteines respectively present in the three SRCR domains of the wild-type human AIM are used for the disulfide bonds in respective SRCR domains. However, the inventors have found that wild-type human AIM contains one isolated cysteine (Solitary Cys) in each of SRCR2 domain and SRCR3 domain, namely, the cysteine at amino acid number 168 and the cysteine at amino acid number 277 of wild-type human AIM shown in SEQ ID NO: 1.

In addition, the inventors predicted the three-dimensional structure of mouse AIM by a similar method. The results of prediction of the three-dimensional structure of wild-type mouse AIM are shown in FIG. 5. The wild-type mouse AIM has 8, 9, 8 cysteines in respective SRCR domains (FIG. 6). It was found that 8 cysteines of those cysteines are used for the disulfide bonds in respective SRCR domains. However, the inventors have found that wild-type mouse AIM contains an isolated cysteine (Solitary Cys) in SRCR2 domain, namely, the cysteine at amino acid number 168 of wild-type mouse AIM shown in SEQ ID NO: 2.

Example 4: Formation of Mutant Human rAIM Multimer

To verify the possibility of the cysteine at amino acid number 168 and the cysteine at amino acid number 277 of wild-type human AIM shown in SEQ ID NO: 1 being involved in the multimerization of wild-type human rAIM, the inventors prepared mutant human rAIM in which the above-mentioned cysteines are substituted with different amino acids. First, to maintain the function of wild-type human rAIM, the amino acid to be used for substitution was studied. Since cysteine is hydrophilic (hydrogen bond can be formed), electric charge 0, and non-aromatic, serine, threonine, asparagine, glutamine were selected as 4 similar amino acids. By comparison of molecular shape and size, since serine had a structure and properties closest to those of cysteine from among the above-mentioned 4 amino acids, serine was selected as amino acid to be used for substitution. The mutant human rAIM was prepared as follows. That is, pCAGGS-human AIM-2CS, pCAGGS-human AIM-3CS, and pCAGGS-human AIM-2/3CS expression vectors that respectively express mutant human AIM (hereinafter to be also referred to as "2CS" in Examples 4, 6, 7) (SEQ ID NO: 3) obtained by substituting codon TGC encoding the cysteine at amino acid number 168 of wild-type human AIM shown in SEQ ID NO: 1 with TCC, mutant human AIM (hereinafter to be also referred to as "3CS") (SEQ ID NO: 4) obtained by substituting codon TGC encoding the cysteine at amino acid number 277 of wild-type human AIM shown in SEQ ID NO: 1 with TCC, and mutant human AIM having both of the aforementioned substitutions (hereinafter to be also referred to as "2/3CS") (SEQ ID NO: 5) were respectively produced. Then, the expression vector was introduced into HEK293T cells by an electroporation method, and each mutant human rAIM expressed transiently by culturing for 3 days was recovered from the culture supernatant. Thereafter, each mutant human rAIM was purified and concentrated using an antibody column by a method similar to that in Example 1. The purified and concentrated wild-type, 2CS, 3CS, 2/3CS human rAIM proteins, each 100 ng, were separated by SDS-PAGE under non-reducing conditions based on the difference in the molecular weights, Oriole staining was performed, and each human rAIM protein was detected.

As a result, 2CS and 3CS obtained by substituting one isolated cysteine present in each of the SRCR2 domain and SRCR3 domain with serine did not form a multimer but formed monomers and dimers alone, like wild-type mouse AIM (FIG. 7). In addition, 2/3CS obtained by co-substituting the above-mentioned isolated cysteine with serine formed monomer alone (FIG. 7). Therefore, it was found that the multimerization of wild-type human rAIM was caused by the cysteine at amino acid number 168 and the cysteine at amino acid number 277 of wild-type human AIM shown in SEQ ID NO: 1. The recovery rate of the final purified rAIM (excluding precipitates from wild-type human rAIM) from the culture supernatant was 32, 52, 53, 61% (average of the recovery rate after 3 times of transient expression and purification) in the order of wild-type, 2CS, 3CS, 2/3CS), and the recovery rate increased in the mutant type.

Example 5: Formation of Mutant Mouse rAIM Dimer

To verify the possibility of the cysteine at amino acid number 168 of wild-type mouse AIM shown in SEQ ID NO: 2 being involved in dimerization of wild-type mouse rAIM, the inventors prepared mutant mouse rAIM in which the above-mentioned cysteine is substituted with serine, as in Example 4. The mutant mouse rAIM was prepared as follows. That is, pCAGGS-mouse AIM-2CS expression vector that expresses mutant mouse AIM (hereinafter to be also referred to as "2CS" in Examples 5, 7) (SEQ ID NO: 6) obtained by substituting codon TGT encoding the cysteine at amino acid number 168 of wild-type mouse AIM shown in SEQ ID NO: 2 with TCT was produced. Then, the expression vector was introduced into HEK293T cells by an electroporation method, and mutant mouse rAIM expressed transiently by culturing for 3 days was recovered from the culture supernatant. Thereafter, mutant mouse rAIM was purified and concentrated using an antibody column by a method similar to that in Example 2. The purified and concentrated wild-type, 2CS mouse rAIM proteins, each 100 ng, were separated by SDS-PAGE under non-reducing conditions based on the difference in the molecular weights, Oriole staining was performed, and each mouse rAIM protein was detected.

As a result, 2CS obtained by substituting one isolated cysteine present in the SRCR2 domain with serine formed only a monomer and did not form a dimer (FIG. 8). Therefore, it was found that dimerization of wild-type mouse rAIM is caused by the cysteine at amino acid number 168 of wild-type mouse AIM shown in SEQ ID NO: 2.

Example 6: Function of Mutant Human rAIM

AIM is taken up by various cells such as macrophages, hepatocytes and adipocytes, and exerts various actions on respective cells. The inventors verified using macrophage cells whether each mutant human rAIM (2CS, 3CS, and 2/3C) lost the function taken up by the above-mentioned cells by mutation. FITC labeling was performed on wild-type and each mutant (2CS, 3CS, and 2/3C) human rAIM using fluorescein-4-isothiocyanate (Dojindo Laboratories). The labeling rate of each human rAIM was similar. Thereafter, each human rAIM was co-cultured for 30 min with F4/80-positive macrophages isolated from the abdominal cavity of AIM-deficient mice in DMEM containing 5% FBS at a concentration of 20 μg/mL, and the human rAIM uptake reaction was performed. The cells were collected and washed, the intracellular uptake of each rAIM was analyzed by measuring the FITC mean fluorescence intensity in F4/80-positive macrophages by a flow cytometer (BD FACSCelesta).

As a result, the uptake of each mutant human rAIM into macrophages was not attenuated as compared to wild-type human rAIM. Therefore, it is considered that each mutant human rAIM was not functionally attenuated. On the contrary, interestingly, 2CS was uptaken by macrophages more than wild-type AIM (FIG. 9).

Example 7: Formation of Complex of Wild-Type or Mutant rAIM and IgM Pentamer

HEK293T cells forcibly expressing IgM and J chain, and HEK293T cells forcibly expressing wild type or mutant (2CS) rAIM were co-cultured for 24 hr, and the proteins contained in the culture supernatant were separated by SDS-PAGE under non-reducing conditions. Then, the protein separated on the membrane filter was transcribed, and whether rAIM and IgM pentamer formed a complex was verified using anti-AIM (a-AIM) antibody or anti-IgM (a-IgM) antibody (mouse (FIG. 10A), human (FIG. 10B)). As a result, in both mouse and human, wild-type rAIM bound to IgM, but 2CS did not bind to IgM.

INDUSTRIAL APPLICABILITY

The mutant AIM of the present invention has the function equivalent to that of the wild-type AIM, or has an improved function, and is characterized in that it does not multimerize when expressed as a recombinant AIM. By the absence of multimerization, recombinant AIM does not precipitate by insolubilization and, as a result, the recovery rate of recombinant AIM is improved and the risk associated with in vivo administration is avoided. Furthermore, when administered to a living body, the mutant AIM of the present invention does not form a complex with an IgM pentamer and thus is not inactivated, and can prevent a decrease in the titer. This application is based on a patent application No. 2017-220733 filed in Japan (filing date: Nov. 16, 2017), the contents of which are incorporated in full herein.

The invention claimed is:

1. A mutant human apoptosis inhibitor of macrophage (AIM) comprising an amino acid sequence of any one of the following (a) to (d) and having an activity of wild-type human AIM:
   (a) an amino acid sequence wherein cysteine at amino acid number 168 of the amino acid sequence shown in SEQ ID NO: 1 is substituted with another amino acid,
   (b) an amino acid sequence wherein cysteine at amino acid number 277 of the amino acid sequence shown in SEQ ID NO: 1 is substituted with another amino acid,
   (c) an amino acid sequence wherein cysteine at amino acid number 168 of the amino acid sequence shown in SEQ ID NO: 1 is substituted with another amino acid, and an amino acid sequence wherein cysteine at amino acid number 277 of the amino acid sequence shown in SEQ ID NO: 1 is substituted with another amino acid,
   (d) an amino acid sequence further comprising deletion, addition, insertion or substitution of one to 5 amino acids or a combination thereof at a position other than the cysteines present in the amino acid sequence of any one of (a) to (c) and the substituted another amino acid of any one of (a) to (c).

2. The mutant human AIM according to claim 1, wherein said another amino acid of subparts (a)-(d) is an amino acid selected from the group consisting of asparagine, glutamine, serine, and threonine.

3. The mutant human AIM according to claim 1, wherein said another amino acid of subparts (a)-(d) is serine.

4. A mutant mouse apoptosis inhibitor of macrophage (AIM) comprising an amino acid sequence of any one of the following (a) to (c) and having an activity of wild-type mouse AIM:
   (a) an amino acid sequence wherein cysteine at amino acid number 168 of the amino acid sequence shown in SEQ ID NO: 2 is substituted with another amino acid,
   (b) an amino acid sequence having a percent identity of not less than 98% with the amino acid sequence of (a), wherein the amino acid sequence retains the cysteines present in the amino acid sequence of (a) and the substituted another amino acid at amino acid number 168, or
   (c) an amino acid sequence further comprising deletion, addition, insertion or substitution of one to five amino acids or a combination thereof at a position other than cysteines present in the amino acid sequence of (a) and the substituted another amino acid of (a).

5. The mutant mouse AIM according to claim 4, wherein said another amino acid of subparts (a)-(c) is an amino acid selected from the group consisting of asparagine, glutamine, serine, and threonine.

6. The mutant mouse AIM according to claim 4, wherein said another amino acid of subparts (a)-(c) is serine.

7. A pharmaceutical composition comprising the mutant human AIM according to claim 1.

8. A pharmaceutical composition comprising the mutant human AIM according to claim 2.

9. A pharmaceutical composition comprising the mutant human AIM according to claim 3.

10. A pharmaceutical composition comprising the mutant mouse AIM according to claim 4.

11. A pharmaceutical composition comprising the mutant mouse AIM according to claim 5.

12. A pharmaceutical composition comprising the mutant mouse AIM according to claim 6.

* * * * *